(12) United States Patent
Clark et al.

(10) Patent No.: US 6,491,519 B1
(45) Date of Patent: *Dec. 10, 2002

(54) FORCE GENERATING DEVICE USEFUL IN ORTHODONTIC APPLIANCES

(75) Inventors: William J. Clark, Fife (GB); Thomas A. Trinco, Jr., Evergreen, CO (US); David E. Watt, Boulder, CO (US)

(73) Assignee: RMO, Inc., Denver, CO (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/079,869

(22) Filed: May 15, 1998

Related U.S. Application Data

(63) Continuation-in-part of application No. 08/438,761, filed on May 11, 1995, which is a continuation-in-part of application No. 08/235,176, filed on Apr. 29, 1994, now Pat. No. 5,443,384.

(51) Int. Cl.[7] .................................................. A61C 3/00
(52) U.S. Cl. ............................................ 433/18; 433/5
(58) Field of Search .................................. 433/5, 6, 7, 18, 433/19, 21, 22, 24

(56) References Cited

U.S. PATENT DOCUMENTS

| 787,861 A | * | 4/1905 | Shelp ....................... 433/18 X |
|---|---|---|---|
| 1,137,298 A | | 4/1915 | Walker |
| 1,142,467 A | | 6/1915 | Walker |
| 1,217,374 A | | 2/1917 | Walker |
| 2,334,894 A | | 11/1943 | Atkinson ....................... 32/14 |
| 2,580,042 A | | 12/1951 | Paus ............................. 32/14 |
| 3,293,747 A | | 12/1966 | Denholtz ....................... 32/14 |
| 3,762,050 A | | 10/1973 | Dal Pont ..................... 32/14 A |
| 3,772,789 A | * | 11/1973 | De Weoskin .................. 433/5 |
| 3,815,238 A | | 6/1974 | Wallshein ................... 433/5 X |
| 3,997,970 A | | 12/1976 | Hodgson ..................... 32/14 R |
| 4,038,754 A | | 8/1977 | Armstrong .................... 433/5 |
| 4,192,069 A | | 3/1980 | McAndrew ................. 433/21 |
| 4,202,100 A | | 5/1980 | Förster ......................... 433/7 |
| 4,245,986 A | | 1/1981 | Andrews ...................... 433/5 |
| 4,354,834 A | | 10/1982 | Wilson ....................... 433/21 |
| 4,373,913 A | | 2/1983 | McAndrew ................... 433/7 |
| 4,375,355 A | | 3/1983 | Dahan ........................... 433/5 |
| 4,375,962 A | | 3/1983 | Dewoskin ..................... 433/5 |
| 4,406,620 A | | 9/1983 | Kaprelian et al. ............. 433/5 |
| 4,424,031 A | | 1/1984 | Dahan ......................... 433/18 |
| 4,468,196 A | | 8/1984 | Keller ........................ 433/24 |
| 4,509,918 A | | 4/1985 | Clark ............................ 433/5 |
| 4,525,143 A | | 6/1985 | Adams ......................... 433/5 |
| 4,529,382 A | | 7/1985 | Creekmore ................... 433/9 |
| 4,553,934 A | * | 11/1985 | Armstrong et al. ........... 433/5 |

(List continued on next page.)

FOREIGN PATENT DOCUMENTS

| DE | 89 03 611 | 7/1990 |
|---|---|---|
| EP | 0 317 098 A2 | 5/1989 |
| EP | 0 397 533 A2 | 11/1990 |

Primary Examiner—Nicholas D. Lucchesi
(74) Attorney, Agent, or Firm—Sheridan Ross P.C.

(57) ABSTRACT

A force generating device is described which includes an elastomeric force generating member. Preferably the elastomeric member is a elastomeric polymer tube. Each end of the tube can be fitted over collars. Attached to one collar is a piston and formed within the other collar is an orifice for slidably receiving the piston. When compressed, the force generating device will attempt to return to its original undeformed shape thus exerting a force along a longitudinal axis. Preferably, the force generating device is employed in an orthodontic assembly. For example, the force generating device can be employed in an orthodontic assembly for developing a patient's arch.

20 Claims, 22 Drawing Sheets

U.S. PATENT DOCUMENTS

| | | | |
|---|---|---|---|
| 4,583,944 A | 4/1986 | Hanson | 433/22 |
| 4,619,609 A | 10/1986 | Clark | 433/6 |
| 4,708,646 A * | 11/1987 | Jasper | 433/19 |
| 4,764,110 A | 8/1988 | Dougherty | 433/5 |
| 4,815,972 A | 3/1989 | Howe | 433/5 |
| 5,022,855 A | 6/1991 | Jeckel | 433/18 |
| 5,087,196 A | 2/1992 | Polanco | 433/21 |
| 5,167,500 A * | 12/1992 | Miura | 433/7 |
| 5,324,194 A | 6/1994 | Magill | 433/19 |
| 5,401,168 A | 3/1995 | Magill | 433/18 |
| 5,443,384 A | 8/1995 | Clark et al. | |
| 5,545,037 A * | 8/1996 | Takeshi | 433/19 X |
| 5,562,445 A | 10/1996 | DeVincenzo et al. | 433/19 |
| 5,651,672 A * | 7/1997 | Cleary et al. | 433/18 X |

\* cited by examiner

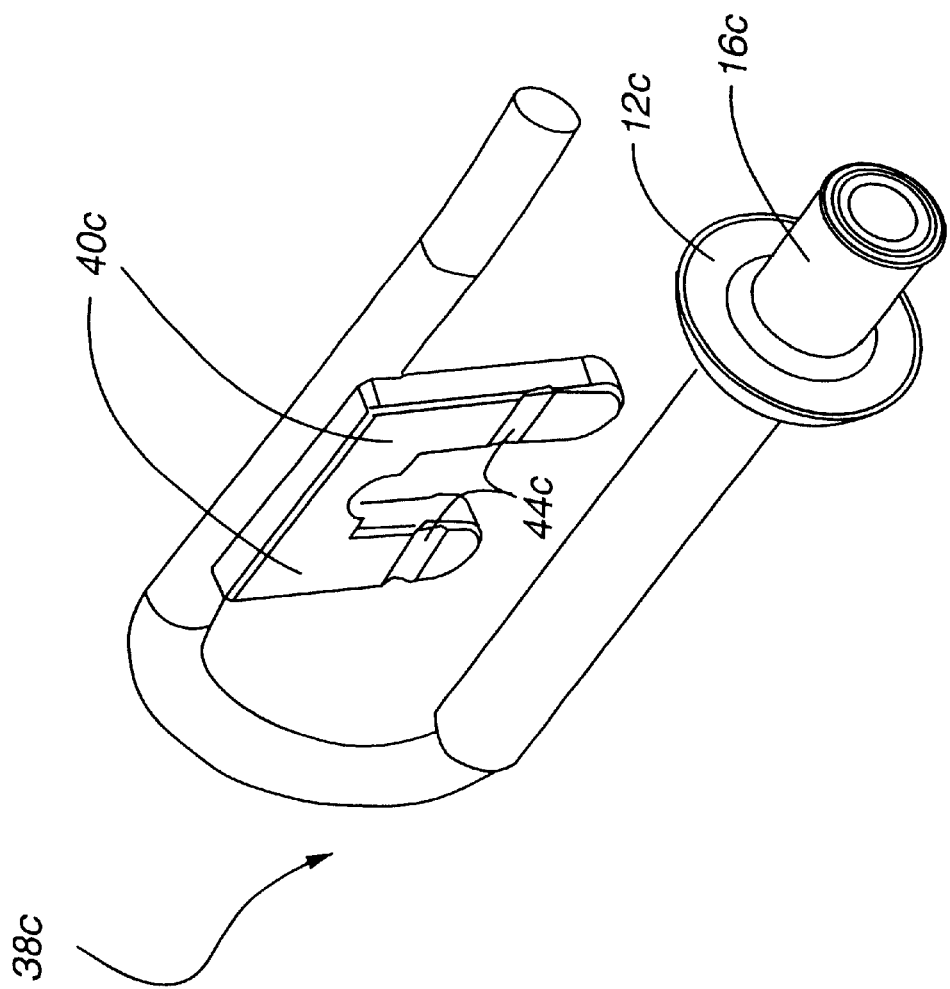

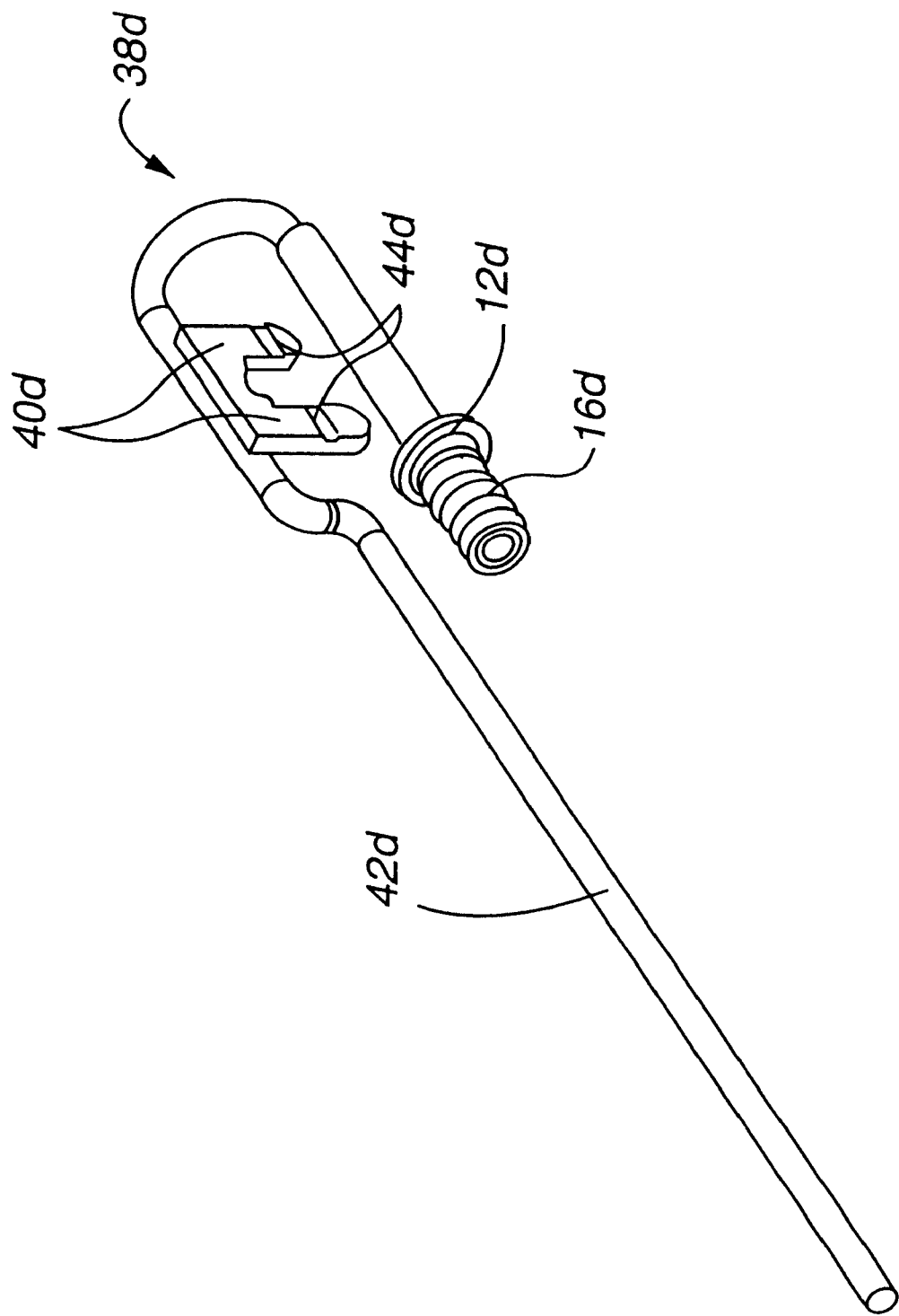

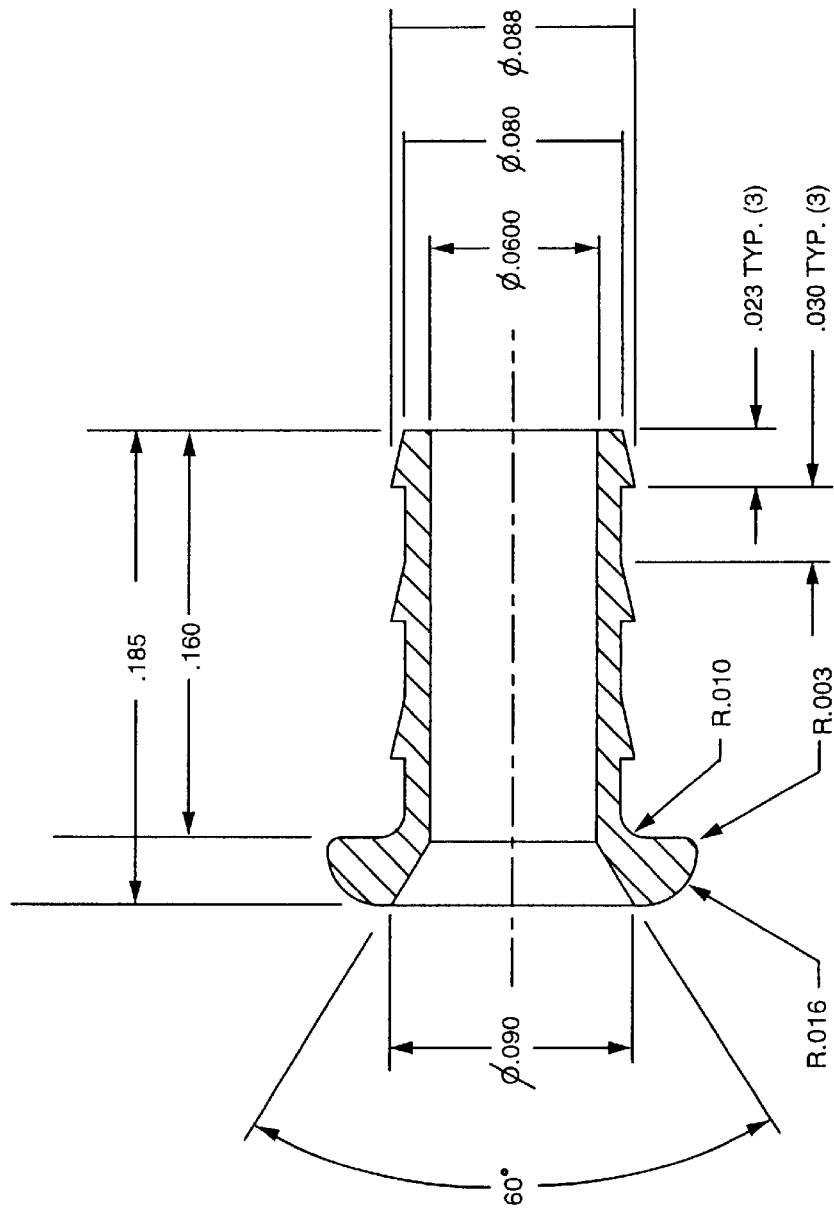
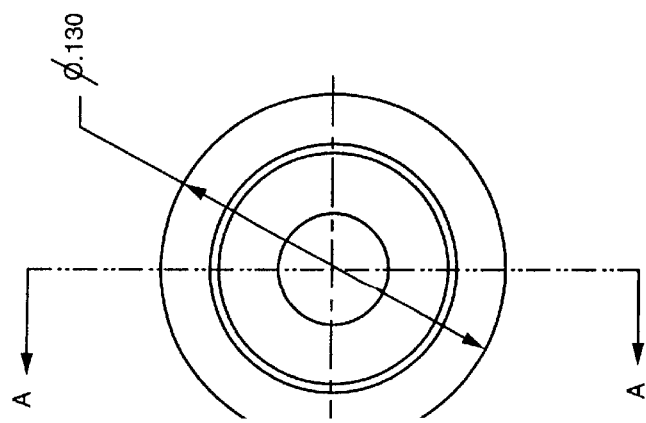
Fig. 6B

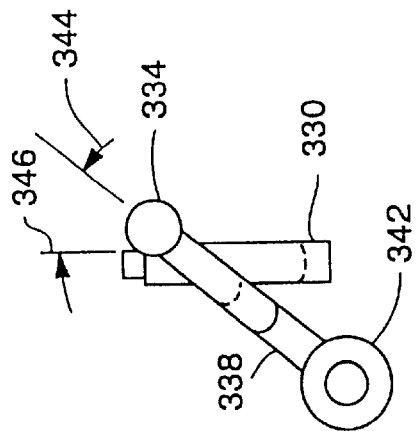
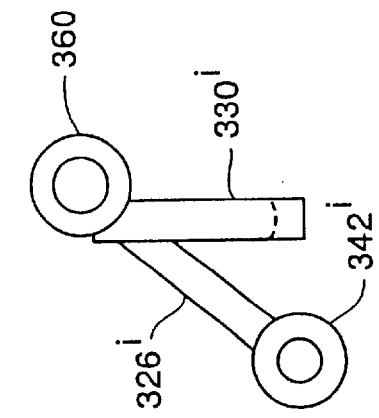
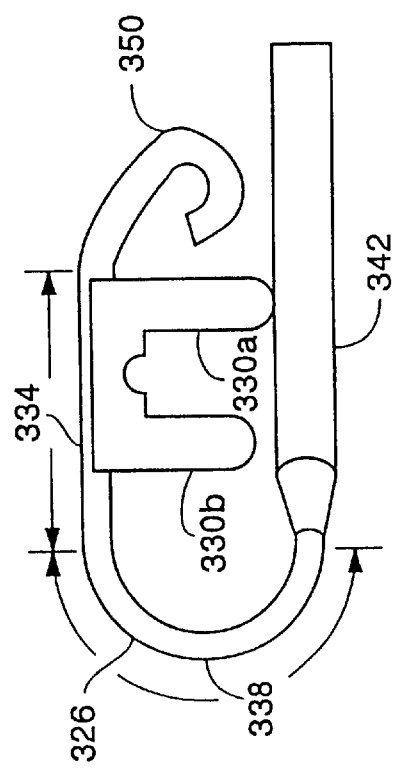
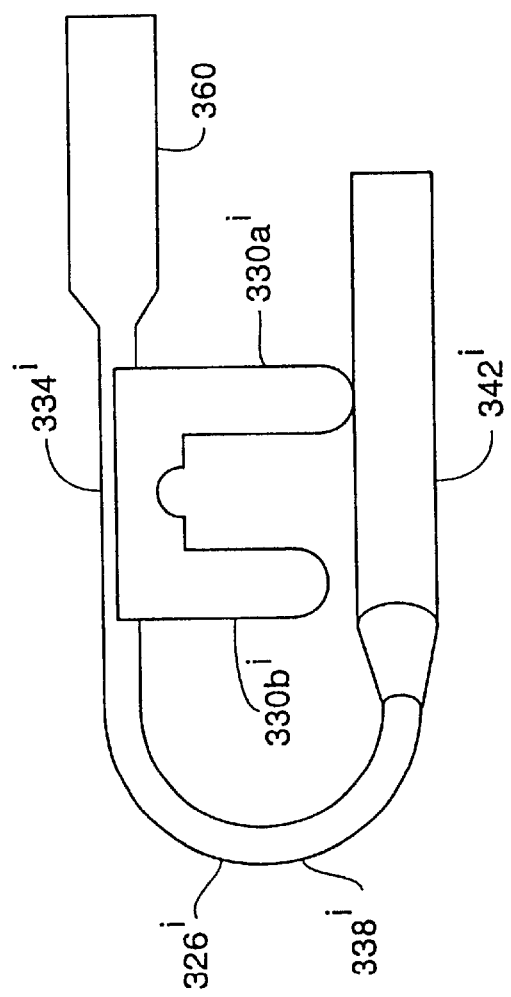

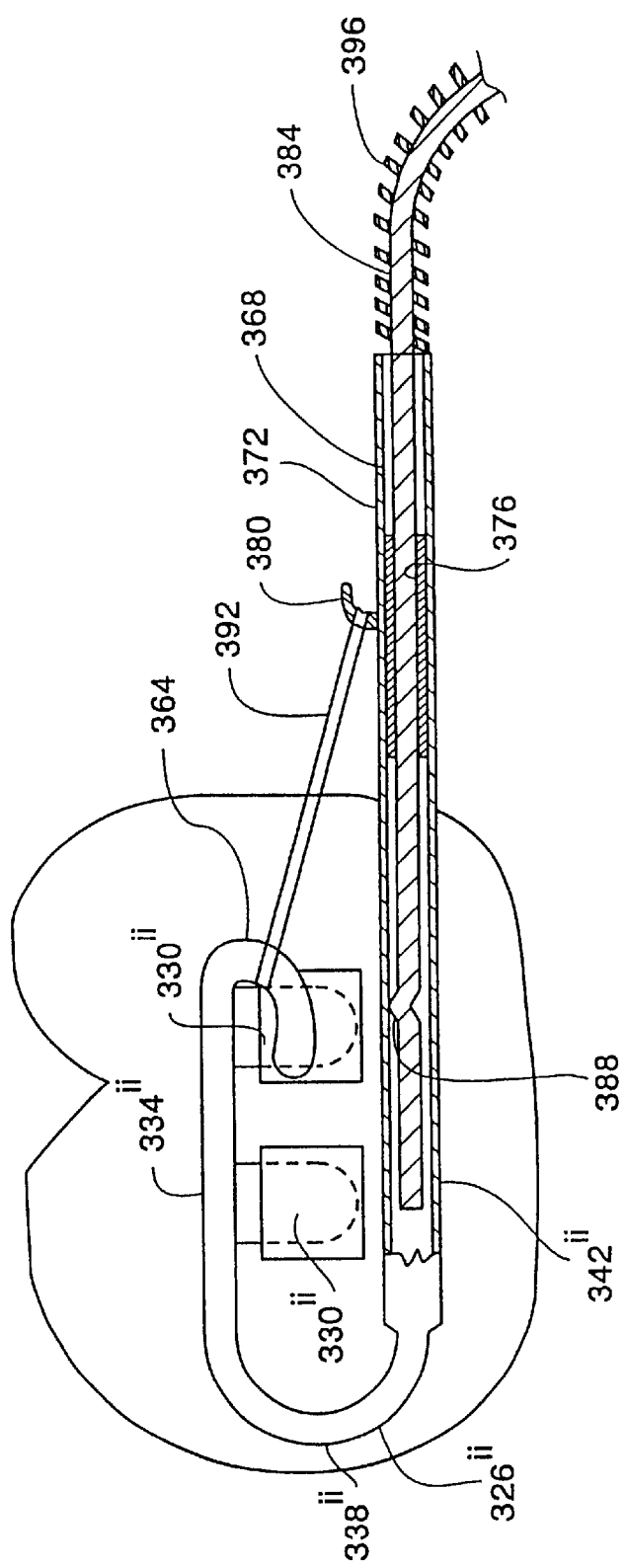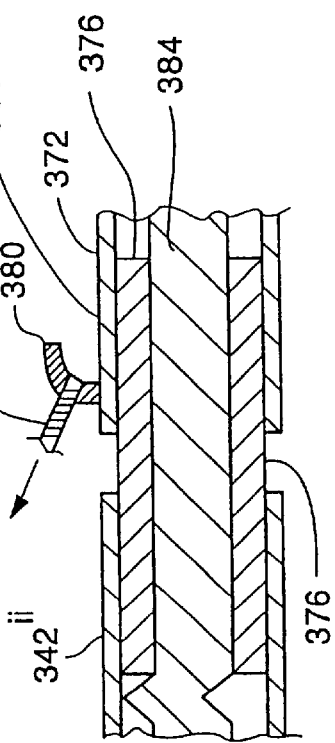
Fig. 15
Fig. 15A

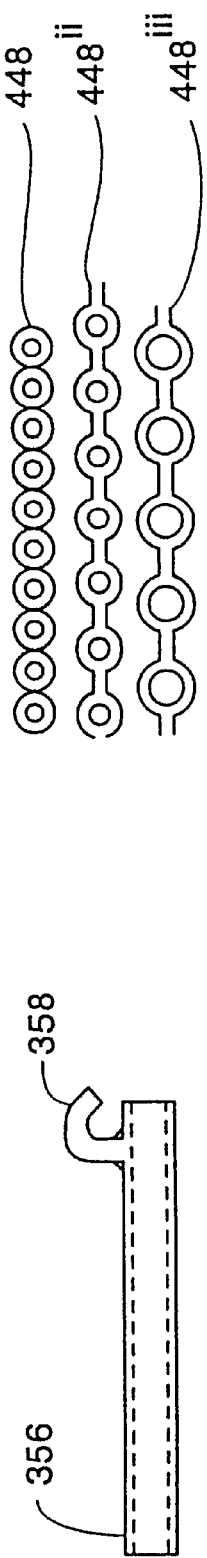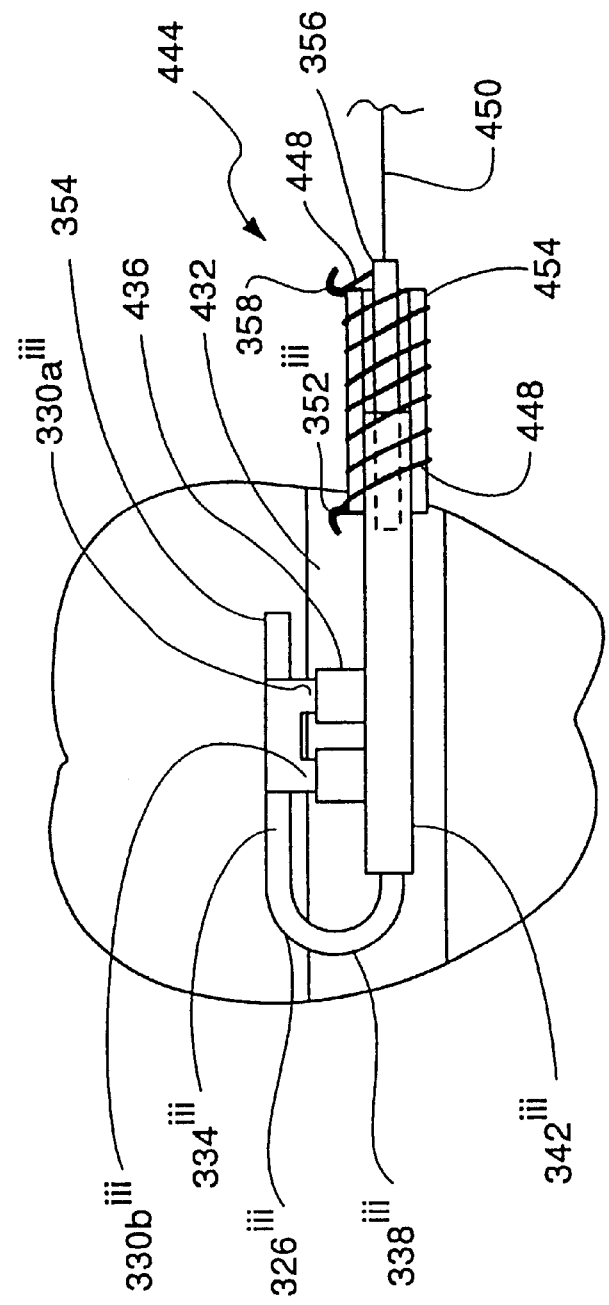

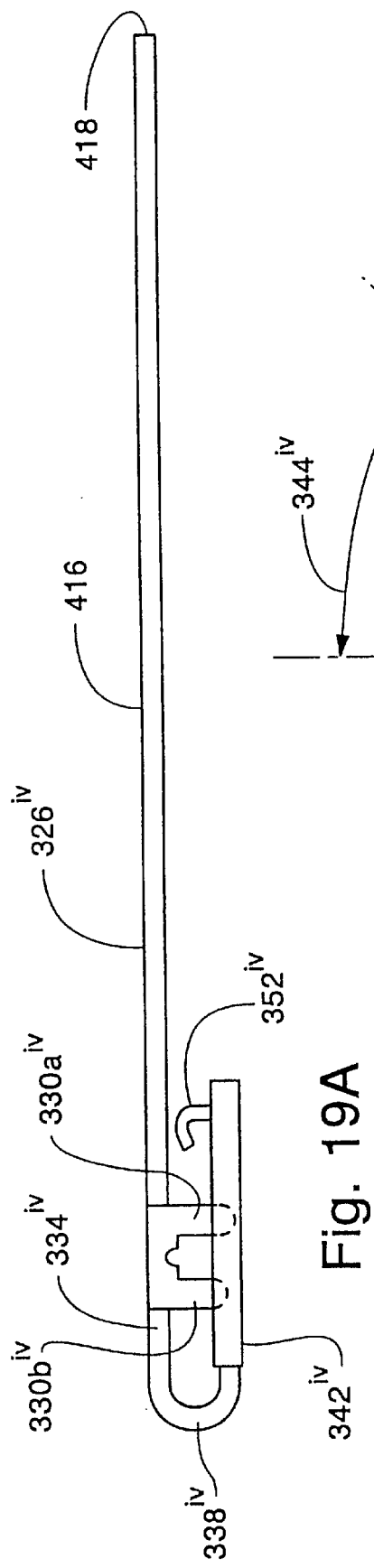
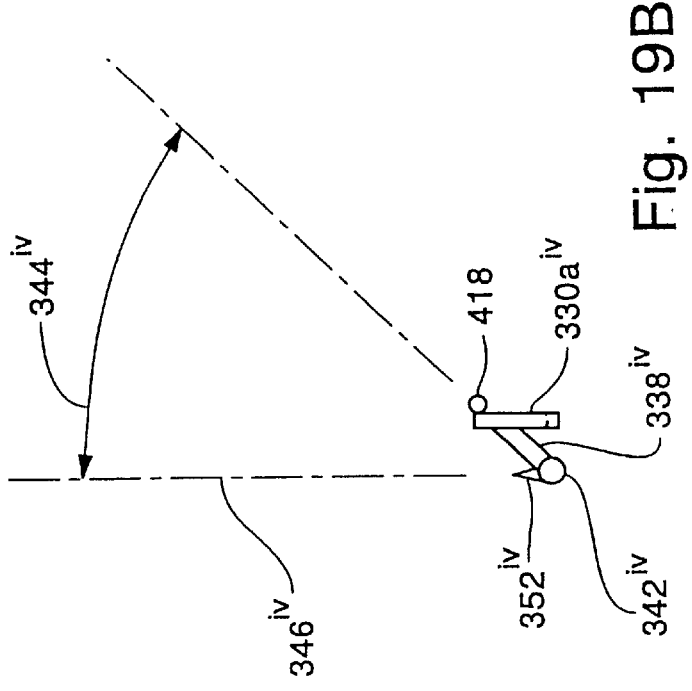
Fig. 19A
Fig. 19B

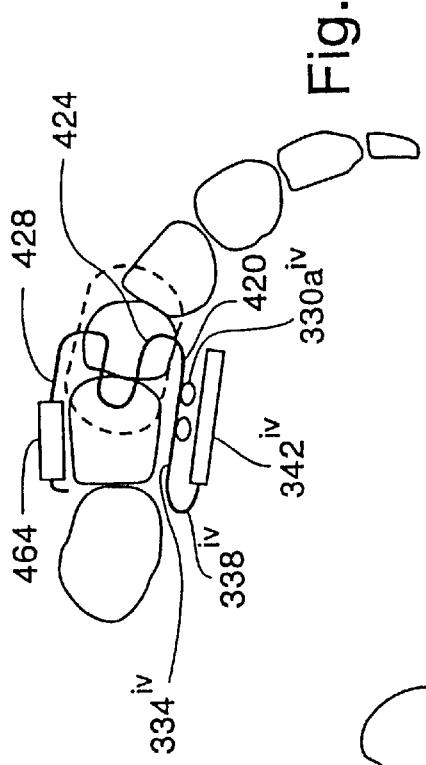
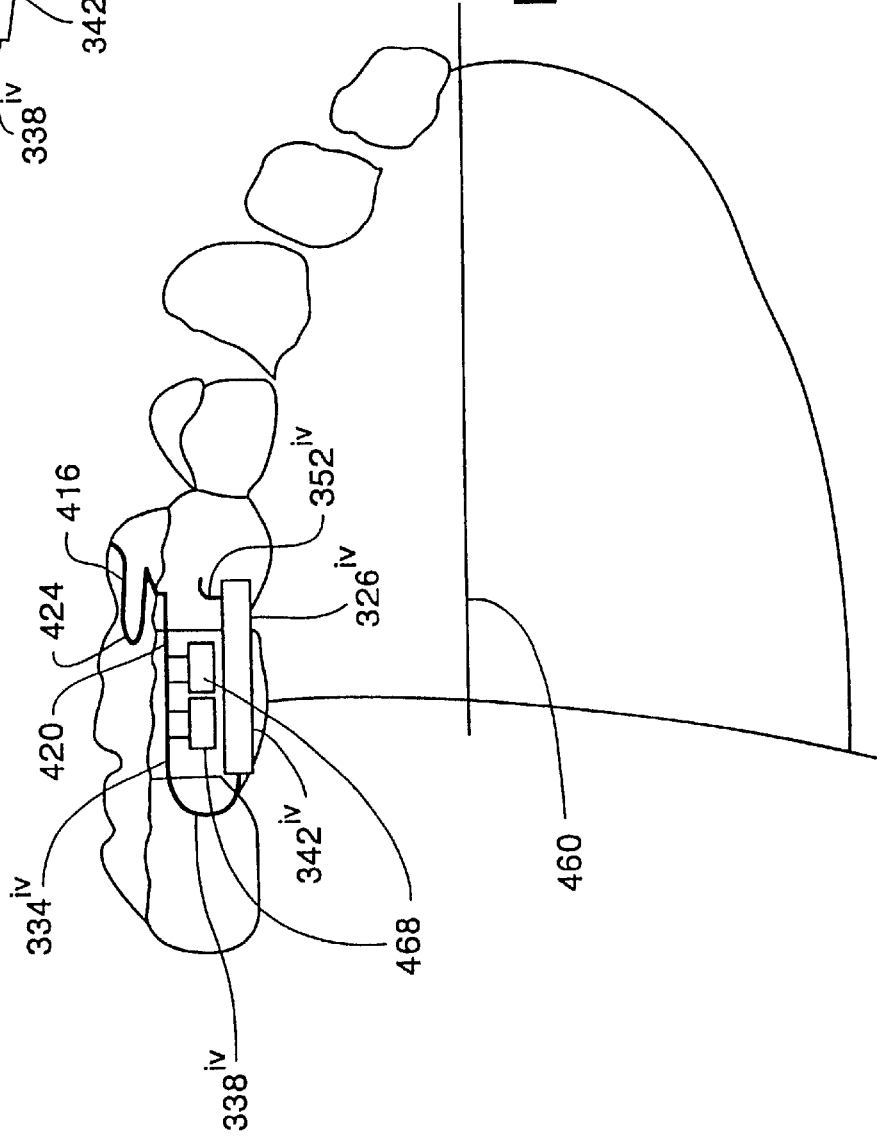

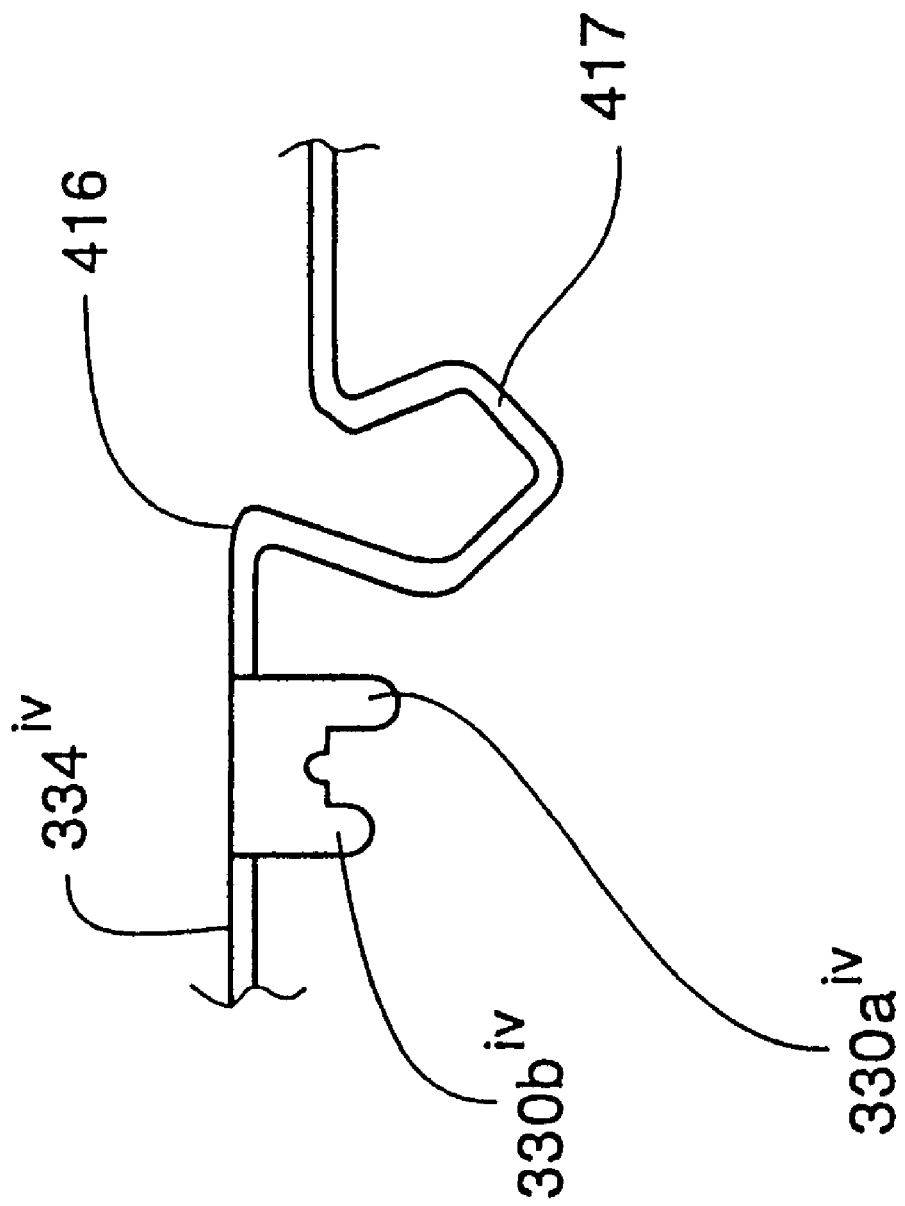

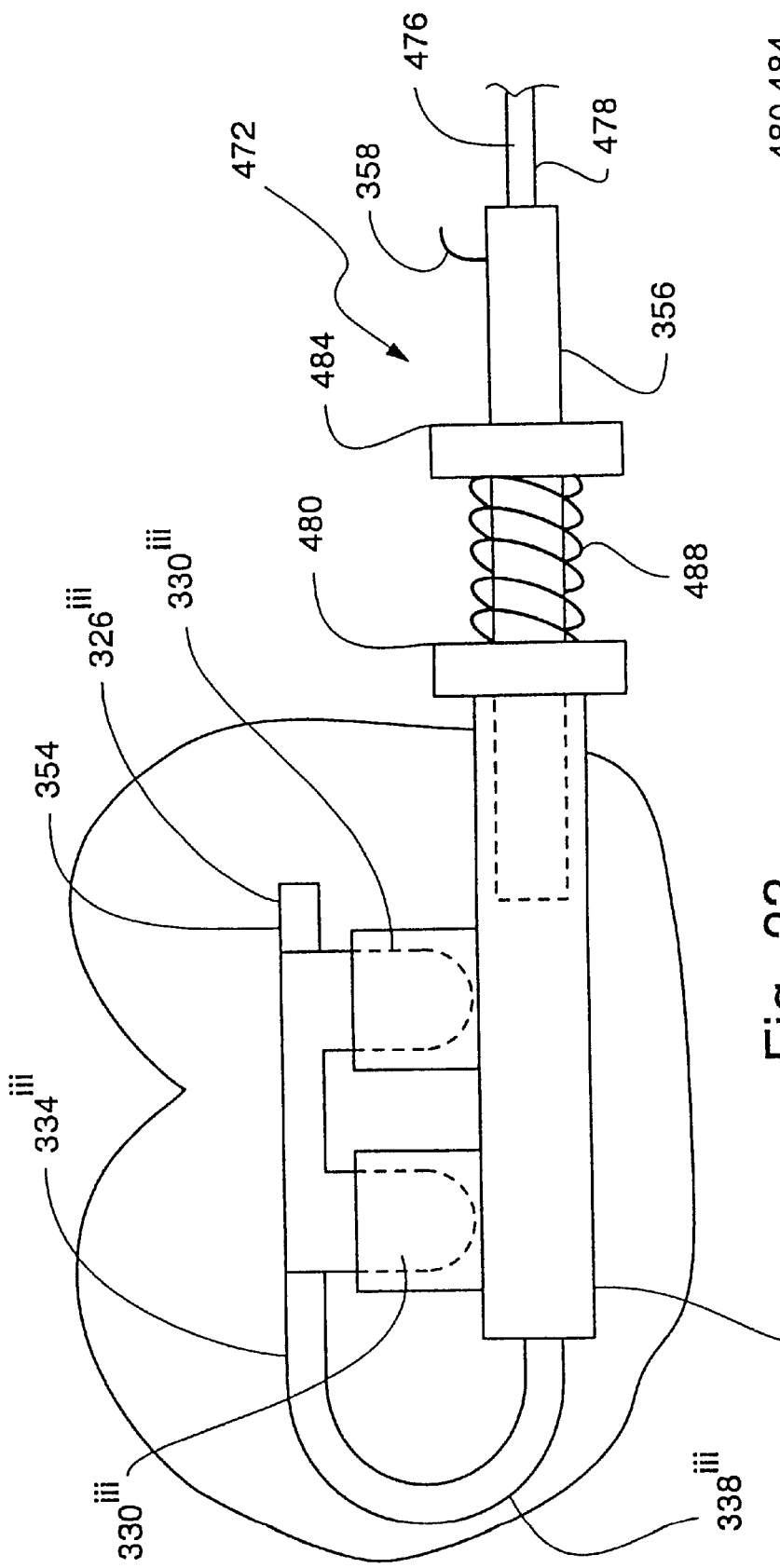
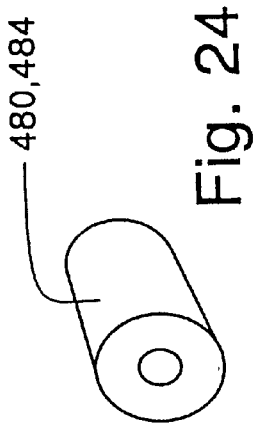
Fig. 23
Fig. 24

FORCE GENERATING DEVICE USEFUL IN ORTHODONTIC APPLIANCES

This application incorporates by reference in their entirety U.S. patent application Ser. No. 08/632,682, filed on Apr. 16, 1996 and entitled "LINGUAL ORTHODONTIC ASSEMBLY FOR ARCH DEVELOPMENT AND COMPONENT PARTS USEFUL THEREWITH", which is a continuation-in-part of abandoned U.S. Pat. application Ser. No. 08/438,761, filed on May 11, 1995 and entitled "LINGUAL ARCH DEVELOPING ORTHODONTIC ASSEMBLY," which is a continuation-in-part Ser, No. 08/235,176 of U.S. Pat. No. 5,443,384, filed Apr. 29, 1994, issued Aug. 22, 1995, and entitled "ORTHODONTIC ASSEMBLY AND METHOD".,

FIELD OF THE INVENTION

The present invention generally relates to the field of force generating devices and, more particularly, force generating devices useful in orthodontic appliances, including appliances useful in developing the arch of an orthodontic patient.

BACKGROUND OF THE INVENTION

Force generating devices, such as springs, elastic bands and archwires, have long been employed in orthodontics. There is a need for improved forced generating devices which provide for ease of use, ease of assembly, ease of adjustment and safety.

SUMMARY OF THE INVENTION

In accordance with the present invention, a force generating device is provided which includes an elastomeric member; a first collar for receiving a first end of the elastomeric member; a second collar for receiving a second end of the elastomeric member; an orifice, which is part of or operationally attached to the first collar, for receiving a piston; and a piston which is slidably engageable into the orifice. The piston is operationally attached to the second collar. When the force generating device is assembled, the elastomeric member operationally connects the first collar and the second collar and the piston is slidably engaged within the orifice.

The force generating member is preferably an elastomeric polymer tube having one end which frictionally engages the outer surface of the first collar and having a second end which frictionally engages the outer surface of the second collar. Preferably, the first collar and the second collar have ribbed outer surfaces in order to enhance the frictional engagement between inner surfaces of the elastomeric polymer tube and the outer ribbed surfaces of the collars. Preferably, the first collar includes a first end stop and the second collar includes a second end stop and the first end of the force generating member is limited in axial movement by the first end stop and the second end of the force generating member is limited in axial movement by the second end stop.

In one embodiment, the force generating device can be operationally interconnected with a tooth of an orthodontic patient. The device for interconnecting preferably includes a "trombone-slide" shaped connector which includes means for attaching the connector to a tooth; a first segment extending at least distally from the means for attaching; a second segment interconnected with the first segment and extending at least gingivally from the first segment; and a third segment interconnected with the second segment and extending at least mesially from the second segment. The means for attaching the connector to a tooth can comprise a band attached to a tooth of an orthodontic patient, the band having a first band tube attached thereto, and a first post slidably interconnectable with the first band tube.

The force generating device can be incorporated into a variety of appliances, including appliances selected from the group consisting of lingual arch developers, labial arch developers and distallizing appliances. For example, in an arch developer the second collar is operationally attached to an arch wire.

The force generating device of the present invention can be employed as part of a connector. Preferably the connector includes as least one post which is removably insertable into a tube on a patient's tooth (e.g, via an orthodontic band attached to the patient's tooth). The connector also includes at least one generally horizontal or mesio-distally extending hollow tube which provides for an interface with an orthodontic appliance (e.g., the force generating device of the present invention, a lingual arch, a palatal expander, a Nance button, a bite block). When the connector interfaces with a force generating device, the hollow tube can be employed as the first collar and/or orifice. Typically, the connector will utilize two generally occlusal-gingivally extending posts (i.e., which are mesio-distally displaced) which are disposable in two generally occlusal-gingivally extending tubes (i.e., which are mesio-distally displaced) associated with a patient's tooth.

For certain orthodontic treatment applications (e.g., mesially-directed arch expansion from the lingual or hereafter lingual arch development) it may be desirable to dispose the noted horizontal tube gingivally. One embodiment which provides a gingivally disposed horizontal tube includes a first segment which is interconnected with the post(s) and extends at least generally distally from the post (e.g., the first segment may also extend occlusally and/or gingivally). A second segment of the connector is interconnected with the first segment and extends at least generally gingivally from the first segment (e.g., the second segment may also extend mesially and/or distally, such as by being generally semicircular, i.e., such that the second segment would initially extend distally and gingivally along an arcuate path, and then mesially and gingivally along an arcuate path). Finally, a third segment of the connector is interconnected with the second segment and extends at least generally mesially from the second segment (e.g., the third segment may also extend occlusally and/or gingivally). At least the mesial-most portion of this third segment is the hollow tube. Preferably, the hollow tube is the orifice which receives the piston of the force generating device. One configuration which is encompassed by the above-described connector is a generally trombone-shaped segment interconnected with the post(s) (either integrally or by some appropriate attachment).

The above-described embodiment may contain a variety of additional features. For instance, a fourth segment may be cantilevered from the first segment and extend mesially beyond the first post a short distance, such as to provide a handle for installing the connector (e.g., extending about 3 mm mesially beyond the mesial-most post). This fourth segment may also be curved to generally follow the surface of the adjacent tooth (e.g., the lingual). The connector may include another generally horizontally disposed or mesio-distally extending tube. One tube may be gingivally disposed as noted above, while this second horizonal tube may be more occlusally disposed. This may be affected by having this second generally horizontal tube extend mesially from the first segment of the connector.

Another feature which may be incorporated into the above-described embodiment is that the third segment may be more lingually disposed than the first segment. This may be effected by having the second segment "spiral" in both a gingival and lingual direction. Moreover, this may be effected by having the second segment be disposed at an angle relative to an occlusal-gingivally extending reference plane (e.g., at an angle of about 45°).

One use for the above-described force generating device and/or connector is in lingual arch development. Lingual arch development involves the application of a generally mesially-directed force on the lingual arch of an orthodontic patient. This may be affected by having a lingual arch slidably interconnected with two anchor teeth, one on each side of a patient's mouth. It may be desirable to limit or control in some respect the mesial advancement of the lingual arch relative to these anchor teeth. The structure of the above-described embodiment may be adapted to provide this feature without adversely affecting performance of the lingual arch developer by interconnecting the force generating device of the present invention with the above-noted connector.

The above-described connector may be adapted for use in conjunction with other types of orthodontic treatments. In some cases it may be desirable to incorporate a fourth segment which is cantilevered from the first segment and extends mesially a distance whereby if this fourth segment were adapted to the lingual of a patient (e.g., bent to follow the lingual of the patient's corresponding dentition), the free end of the fourth segment would be at least at and preferably slightly beyond the midline of the patient's dentition. One use of this type of fourth segment is to adapt the fourth segment to the lingual of the desired dentition of the orthodontic patient. Installing a connector on each side of the patient's mouth then results in two of these fourth segments being in an overlapping relation at generally the patient's midline. In this configuration, one may attach the two free ends of the two fourth segments together. Various types of bends may then be placed in one or both of these fourth segments to apply desired orthodontic treatment forces to the corresponding dentition. Another option is to let the free ends of the two fourth segments act independently of each other by not joining them together such that both remain independently active. In this overlapping arrangement, it should be appreciated that the fourth segment could be bent so as to be more gingivally disposed as well if such would be desirable or required for certain applications.

Another use of the above-noted type of fourth segment when a connector is installed on each side of the patient's mouth is to bend both fourth segments in a manner such that their respective free ends are disposed generally proximate to the forward portion of the orthodontic patient's mouth but at a location which is away from the teeth. In this position the fourth segments may provide a frame of sorts for a frontal anchorage which does not adversely affect tooth position since the anchorage is not directly on the patient's tooth or teeth (e.g., an acrylic may be molded over the free end portions of the two fourth segments, which acrylic will engage the patient's soft tissue but not the patient's teeth to provide the desired anchorage for other orthodontic treatment forces being applied to the patient). Mounting a connector on each side of the patient's upper dentition will further allow the fourth segments to be bent to extend up to the vault of the patient's palate. This provides a desirable mounting for certain palatal expanders.

Another aspect of the present invention relates to a lingual orthodontic assembly. A generally mesio-distally extending tube is lingually attached to a tooth on each side of the orthodontic patient's mouth. This may be provided by installing one of the above-described connectors on each side of the patient's mouth. As such, it should be appreciated that various aspects of the present invention may be used combinatively as well as singularly. The ends of a lingual arch are typically compressed toward each other (e.g., for arch expansion) and inserted into the associated mesio-distally extending tube such that the arch exerts an expansive (relative to the patient's midline) force on the patient's corresponding dentition. Two mountings (e.g., hooks) are provided on at least one side of the orthodontic assembly. One of these mountings is associated with the tooth on which one of the mesio-distally extending tubes is installed. The other may be associated with another tooth on the same side of the patient's mouth, but is more preferably associated with the lingual arch. A torquing member is attached to and extends between each of these mountings to apply a torquing force to at least the tooth on which the mesio-distally extending tube is installed. This may be affected by wrapping the torquing member about the horizontal tube and/or the lingual arch. Appropriate torquing members include elastics (e.g., energy chain elastics). In the case where the above-described connector is used, the torquing member would be wrapped around both the third segment of the connector and then the sectional. It should be appreciated that this aspect of the invention could be incorporated on only one side of the patient's mouth, but would preferably be used on both sides of the patient's mouth.

BRIEF DESCRIPTION OF THE DRAWINGS

FIG. 4 illustrates the "trombone-shaped" connector with dual posts with detents.

FIG. 5A illustrates a connector with an upper extension.

FIG. 6B illustrates a ribbed collar.

FIG. 11 is a side view (looking labially) of another embodiment of an orthodontic connector, such as for a lingual arch developer.

FIG. 12 is an end view (looking distally) of the connector of FIG. 11.

FIG. 13 is a side view (looking labially) of another embodiment of an orthodontic connector, such as for a lingual arch developer.

FIG. 14 is an end view (looking distally) of the connector of FIG. 13.

FIG. 15 is a cross-sectional view (looking labially) of another embodiment of a connector for a lingual arch developer.

FIG. 15A is a partial cross-sectional view of the "resistance" position of the ligature assembly from the connector of FIG. 15.

FIG. 18A is a side view of an end section for use with any of the above-described orthodontic connectors.

FIG. 18B is a side view of an assembly which ligates the lingual arch and which also generates a torquing force.

FIG. 18C are views of various embodiments of elastics for use in the ligature assembly of FIG. 18B.

FIGS. 19A–B are views of another embodiment of an orthodontic connector for providing an interface between a tooth and an orthodontic appliance, such as a lingual arch developer.

FIGS. 20A–B are views of one application for the connector of FIGS. 19A–B.

FIG. 21 is a side view of another application of the connector of FIGS. 19A–B.

FIG. 23 is a side view of another embodiment of a lingual arch developer which utilizes magnets.

FIG. 24 is a perspective view of one embodiment of a magnet which may be used with the lingual arch developer of FIG. 23.

DETAILED DESCRIPTION

As noted above, lingual arch development may be affected utilizing a lingual arch which accommodates the exertion of a generally mesially directed force lingually on a patient's arch and which comprises another aspect of the present invention. That is, this aspect of the present invention generally relates to lingual arch development and more specifically relates to lingual arches which accommodate the application of a generally mesially directed force lingually to a patient's arch. A number of new orthodontic assemblies, including new lingual arch designs, as well as orthodontically-related procedures, have evolved which are useful in utilizing this application of a mesially-directed treatment force to the lingual arch of an orthodontic patient.

In one embodiment of this lingual arch development aspect of the present invention, such relates to the application of a generally mesially-directed force to a generally U-shaped lingual arch, such as the lingual arch configurations discussed below. The lingual arch is preferably slidably interconnected with each side of a jaw of an orthodontic patient undergoing treatment. For instance, at least one horizontal tube may be attached to teeth on opposite sides of the jaw being treated. The mesially-directed force may then be applied to the lingual arch to affect mesial movement of the lingual arch and thus part of the patient's arch relative to at least one reference point(s) (e.g., the teeth on which the tubes are installed which provide an anchor for the application of the mesially-directed treatment force). Appropriate sources for the mesially-directed forces include compression springs and compressible elastomers or tubing (e.g., cylindrical elastomeric polymer tube sections which may be axially compressed).

The force generating device preferably employs an elastomeric tube. For example, the elastomeric tube can be made of any polymer or composite which is compressible and which possesses a memory. As used herein, the term "memory" refers to the property of an elastomeric member which causes it to attempt to return to its original shape after deformation. The material should be biocompatiable, as it will be used in the mouth of a patient. A preferred material is silicone and more preferably, platinum cured silicone. However, any other suitable polymer or composite can be used, including natural (e.g., rubber) and synthetic (e.g., silicone) polymers.

Figure 1:
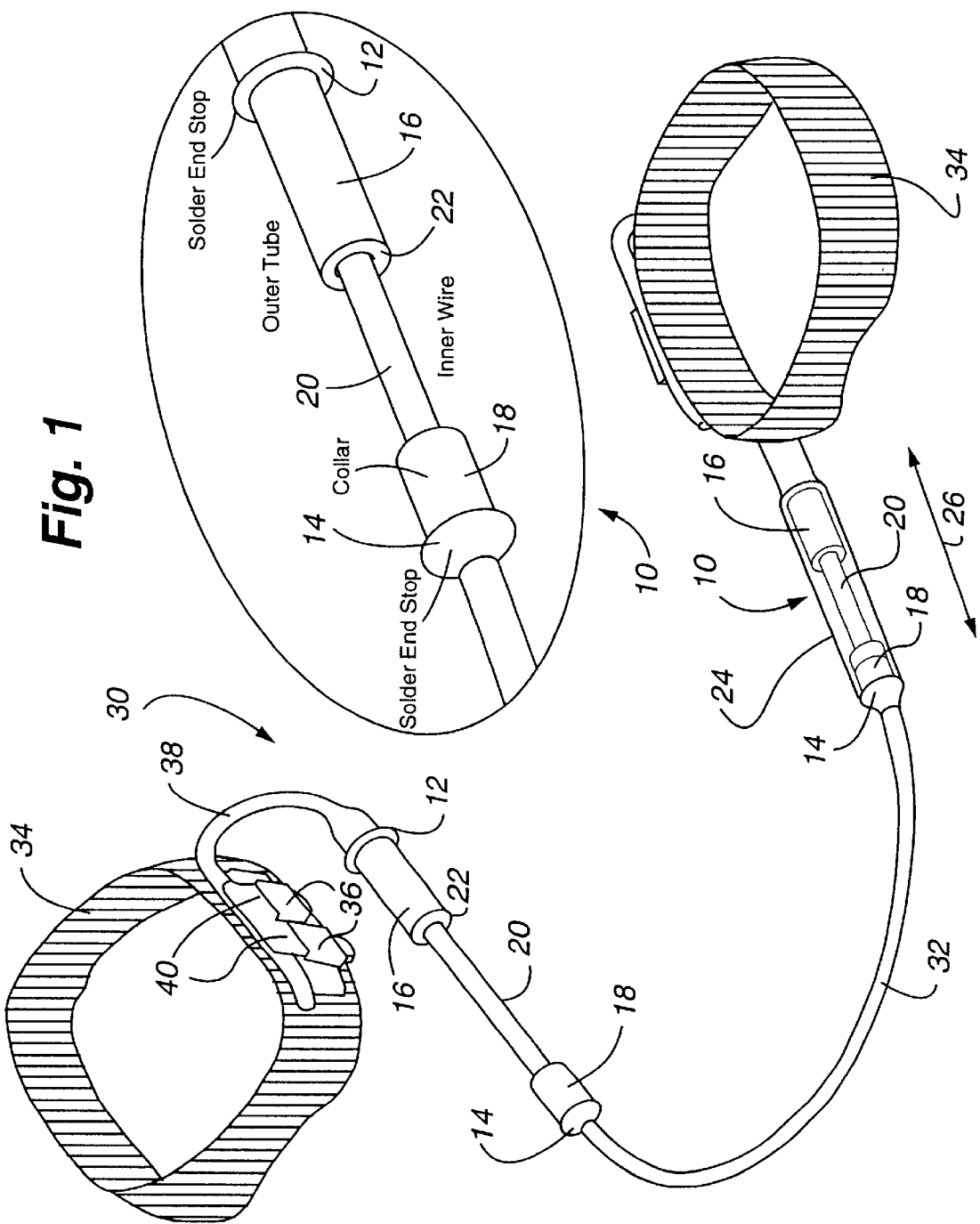
FIG. 1 illustrates a force generating device incorporated into a lingual arch developer and includes a magnified view of the force generating device.
Figure 2:
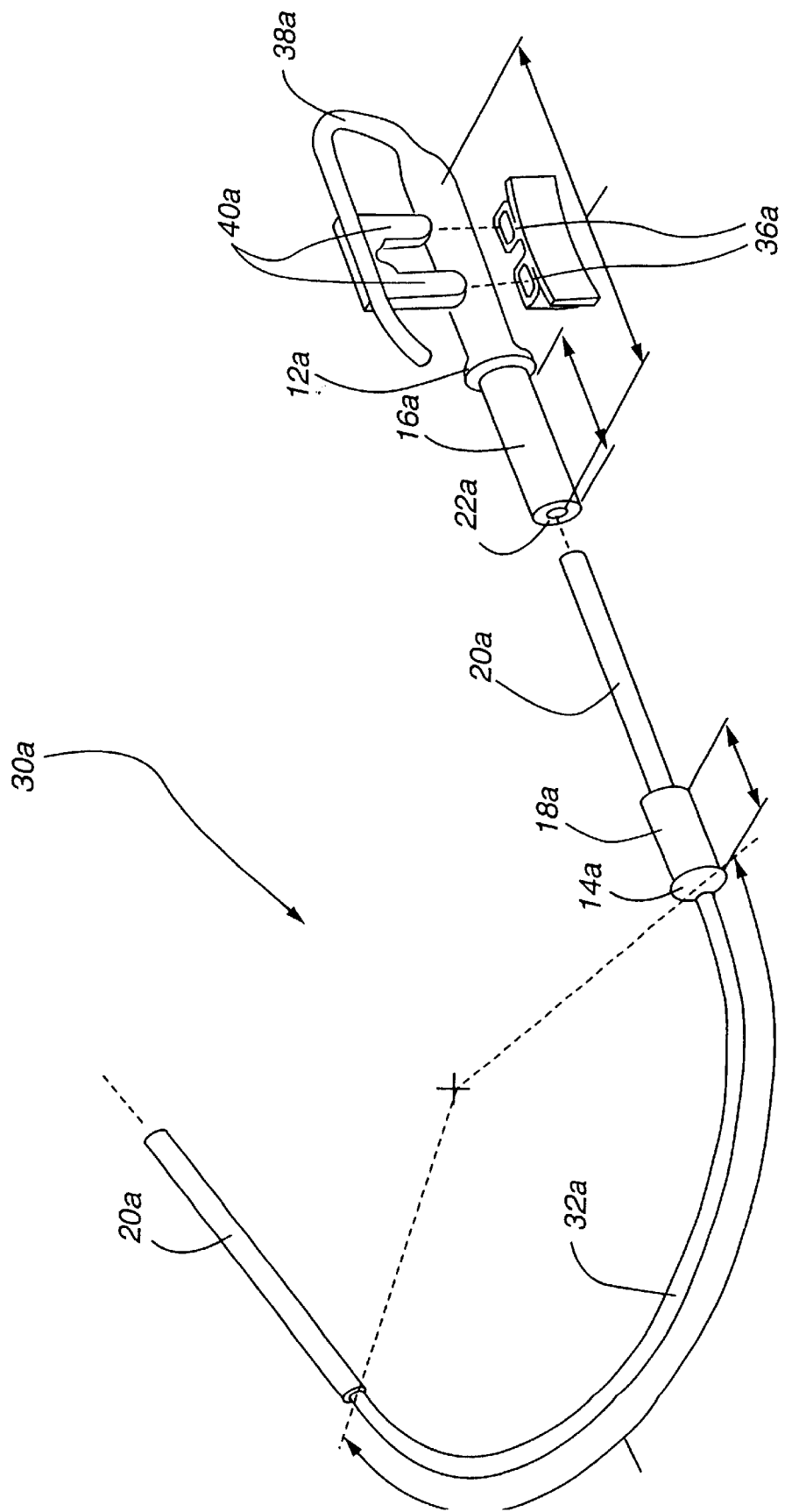
FIG. 2 illustrates a lingual arch developer with a force generating device.
Figure 3:
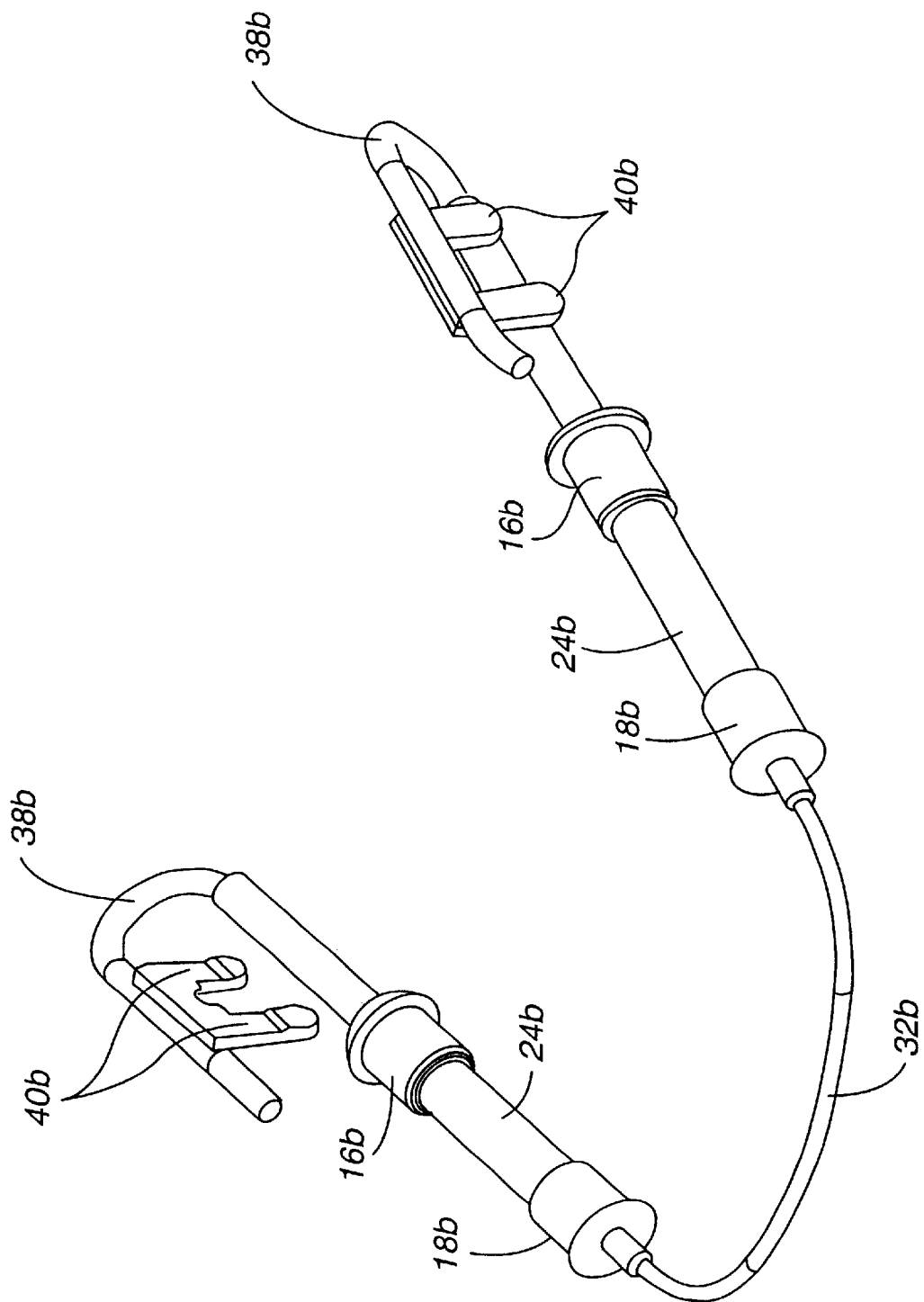
FIG. 3 illustrates a lingual arch developer with a force generating device.

As illustrated in FIGS. 1–6, the force generating device of the present invention includes a first end stop 12 and a second end stop 14. Located adjacent first end stop 12 is first collar 16. Located adjacent second end stop 14 is second collar 18. Preferably, one or both of the collars 16 and 18 are ribbed as shown in FIGS. 6A and 6B. Attached to second collar 18 is inner wire 20. Inner wire 20 can be received in outer tube 22. Outer tube 22 is formed by providing a receiving orifice within first collar 16. The force generating tube 24 is positioned in a tight fitting arrangement over first collar 16 and second collar 18 with inner wire 20 received in outer tube 22. Alternatively, as illustrated in FIG. 3, the force generating member 24 can be placed inside collars 16*b* and 18*b*. Collar 16*b* has a further inner orifice (not shown) for receiving the inner wire or piston (not shown). When compressed, the force generating tube 24 will, due to its memory, attempt to return to its original uncompressed configuration, thereby generating a force along the longitudinal axis of the force generating member (see arrow 26).

Figure 5B:
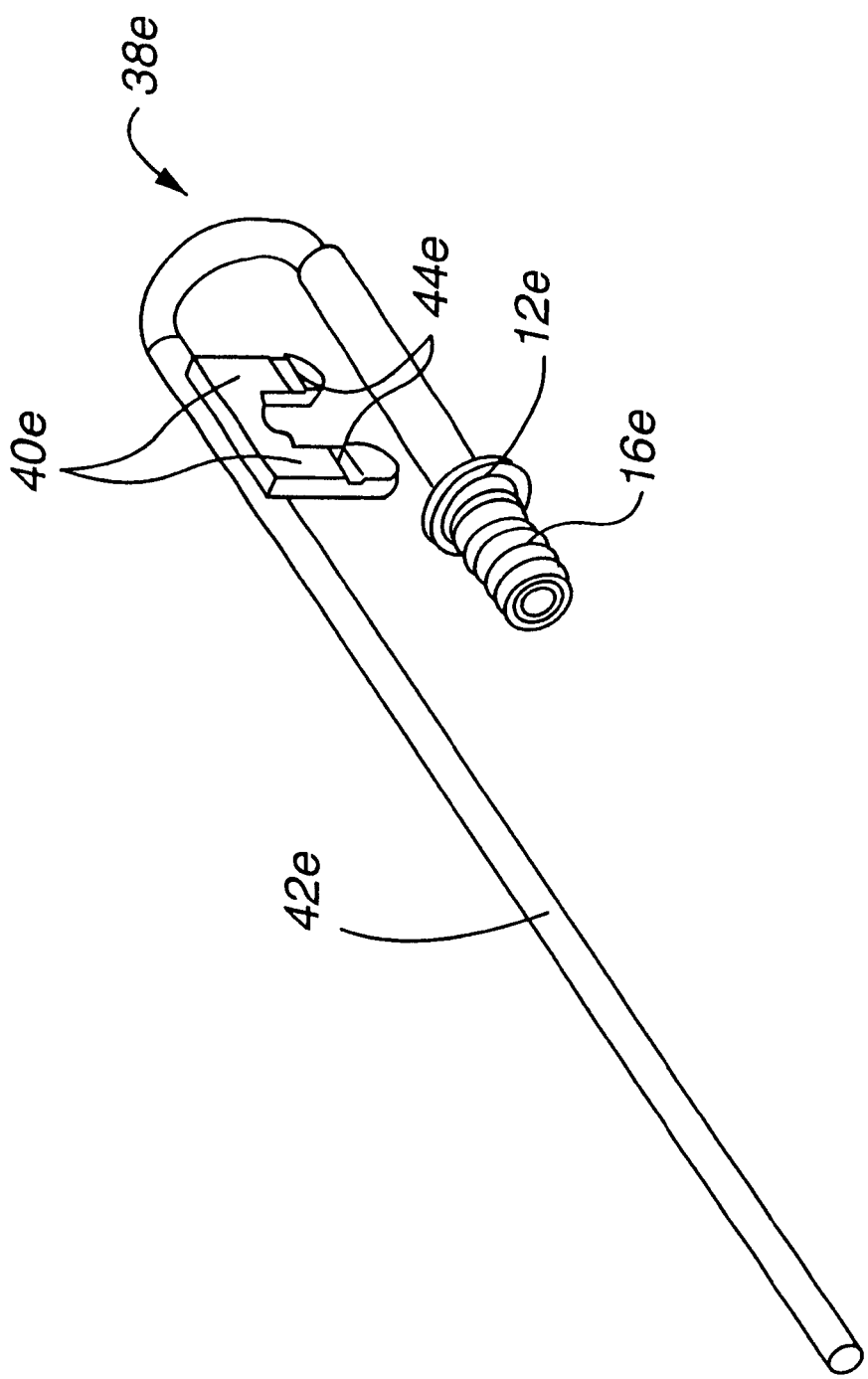
FIG. 5B illustrates another embodiment of a connector with an upper extension.
Figure 6A:
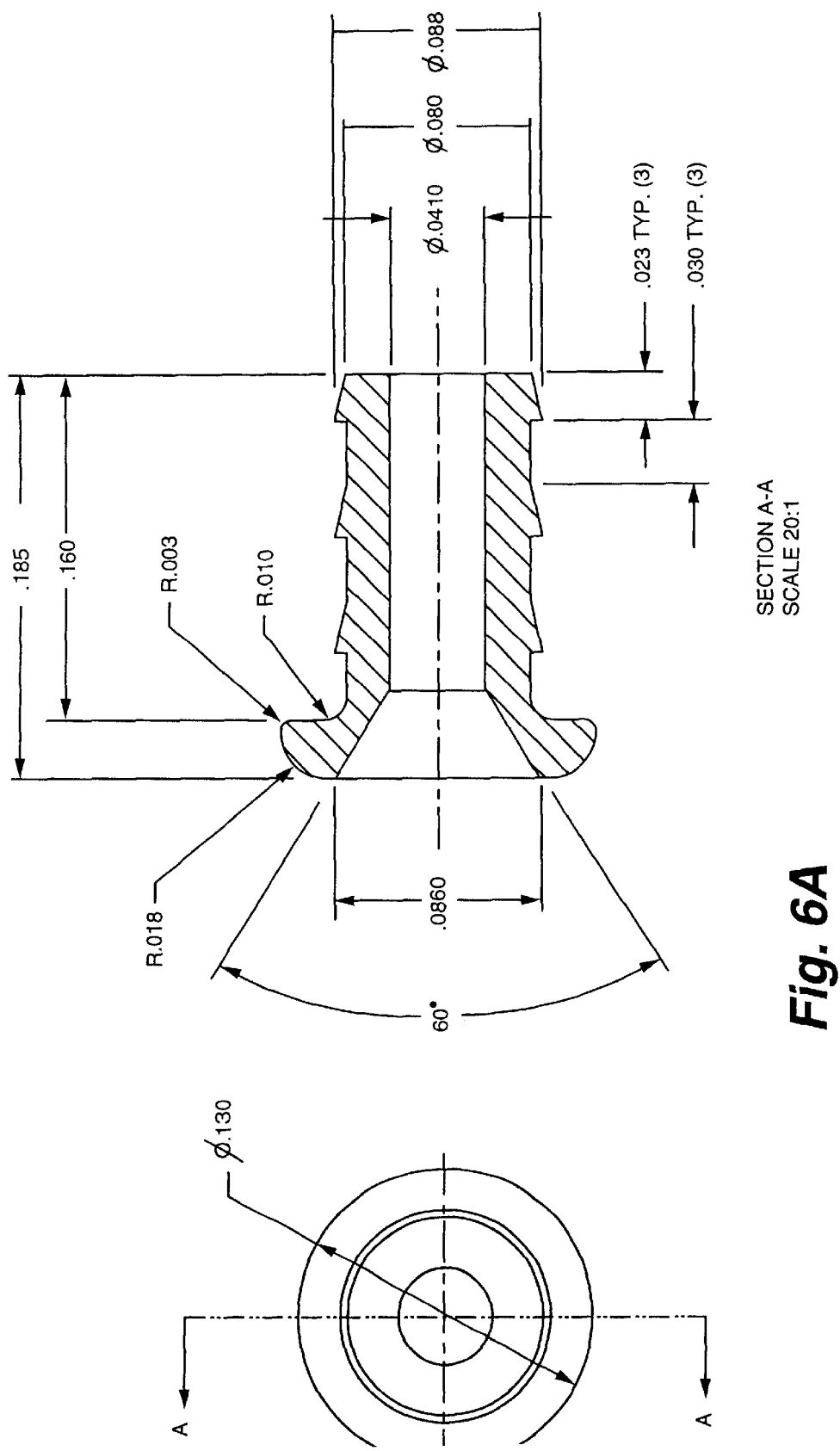
FIG. 6A illustrates a ribbed collar.

In a preferred embodiment, the force generating device 10 is employed in a lingual arch developer 30 as illustrated in FIGS. 1 and 2. Corresponding parts and different embodiments of similar parts have the same number, followed by a lower case letter (e.g. 10, 10*a* etc.). Therefore, the force generating device 10 can generate a force in the anteroposterior direction. In other words, the force is generated along a mesio-distally extending axis. The arch wire 32 employed in a lingual arch developer 30 can also apply desired forces in order to expand the arch of the patient. The lingual arch developer 30 illustrated in FIG. 1 is designed to be inserted on the lingual side of the orthodontic patient's teeth. Bands 34 can be wrapped around, and preferably cemented, to teeth (e.g., molars) on each side of the patient's mouth. Preferably, the bands include a tube or tubes 36. A trombone-shaped connector 38 including posts 40 can be inserted into the tubes 36. The lingual arch developer 30 can be easily assembled and inserted into the patient's mouth. The connectors 38d and 38e shown in FIGS. 5A and 5B, respectively, can further include upper extensions 42d and 42e, respectively, as will be discussed in greater detail below. As shown in FIGS. 4, 5A and 5B, detents 44c, 44d and 44e can be employed on posts 40c, 40d and 40e, respectively, to secure the posts in corresponding tubes, as is more fully disclosed in U.S. Provisional Patent Application Serial No. 60/063,890, filed on Oct. 24, 1997 and entitled "FIXATION MECHANISM FOR POST AND TUBE DENTAL APPLIANCE," which is incorporated herein by reference in its entirety An advantage of the present device is that the force generating tube 24 can also generate a torsional or torquing force. For example, by providing a radial twist to the tube 24 prior to installing the tube 24 over the last collar, the memory of the force generating tube 24 will cause the tube 24 to try to return to its original configuration. This can apply a torquing force to the tooth (not shown) to which the force generating device 10 is attached (e.g. a molar).

An advantage of providing a torquing force to the tooth to which the device 10 is attached is that it helps counteract "tipping" of the anchored tooth. Tipping occurs because the connector band 34 of a device, such as a lingual arch developer 30, is typically attached above the centroid of the attached tooth. Therefore, as forces move the tooth in a buccal direction, the tooth can have a tendency to "tip", i.e., the crown of the tooth may be forced outward to a greater degree than the root. Therefore, the use of a twisted force generating tube 24 can counteract this tipping by providing a torque in the opposite direction.

Alternatively, tipping can be counteracted by using a configuration for the inner wire and the outer receiving tube which prevents relative rotation. For example, if the inner wire and outer tube orifice are non-circular (e.g., square or rectangular) (not shown), tipping can be reduced or eliminated because relative rotation will be reduced or eliminated. In other words, the connector 38 will be restrained from rotating or tipping relative to the inner wire 20. As used herein, the terms "inner wire" and "outer tube" are not limited to circular cross-sectional configurations, but can include other cross-sections (e.g., oval, polygonal, including square, rectangular, triangular, star-shaped, etc.) which prevent relative rotation between the inner wire 20 and outer tube 22.

The force generating device of the present invention can be employed in any device in which an axial force is desired. Examples of orthodontic devices include lingual arch developers, labial arch developers and distillizing appliances. A labial arch developer can be used on the labial side of the teeth to modify an orthodontic patient's arch. A distillizing appliance can be employed to move the molars back in a distal direction to provide greater arch length, i.e. to open up the arch length.

When employed, for example in a lingual arch developer, the entire device including the arch wire, the force generating member, the post and tube connector and the connector band can all be assembled prior to insertion into the patient's mouth. Typically, the band will be cemented to the anchoring teeth, for example, the molars of the patient. Thereafter, adjustments can easily be made by removing the post from the tubes and replacing the force generating tube and making any other necessary adjustments. Typically the force generating tube will be increased in length as treatment progresses in order to expand, or open up the arch.

The initial configuration of a lingual arch developer and the desired length of the force generating tube can be determined relatively easily. For example, a mold can be made of the teeth. A transparent template can then be placed over the mold. The template includes guidelines which assist the orthodontist in determining the correct configuration of the lingual arch developer, as well as the desired length of the force generating (e.g., silicone) tubes. The device can then be fabricated and easily inserted into the patient's mouth. The device is especially useful when combined with the "trombone shaped" post and tube attachment system. This trombone shape provides a greater length in which to accommodate the force generating device. Advantages of the present device are ease of use, ease of assembly and ease of adjustment. In addition, the device reduces the number of parts which can become disconnected and act as small foreign bodies in the mouth.

In another embodiment relating to the lingual arch development aspect of the invention, such as generally directed toward installing lingual arches, preferably such that the above-noted generally mesially-directed forces may be exerted thereon. In one variation, a lingual arch includes at least one helical winding, and preferably at least one helical winding on each of the two sides of the lingual arch relative to a central axis extending therethrough. These helical winding(s) may be used to generate/transmit orthodontic treatment forces, other than a mesially directed force, lingually to the patient's teeth (e.g., expansion forces). The helical winding(s) also allow the mesial section of the lingual arch to be pivoted occlusally relative to the distal section of the lingual arch in a predetermined manner. This facilitates installation of the two distal ends of the lingual arch into horizontal, lingual tubes which are attached to the patient's teeth, typically via an orthodontic band. As will be discussed in more detail, the use of a slidable interconnection between the lingual arch and the horizontal tubes allows the lingual arch to be advanced mesially relative to the anchor teeth on which the tubes are positioned when a mesially directed orthodontic treatment force is utilized.

In another variation, an orthodontic assembly includes a lingual arch in which at least the distal ends thereof are hollow. The assembly further includes at least two gingivally-occlusally extending tubes which are attached to teeth on opposite sides of the mandibular jaw or maxillary jaw of an orthodontic patient (e.g., at least one tube on one tooth on one side of the patient's jaw, and at least one tube on one tooth on the other side of the patient's jaw). The interconnection between this lingual arch and the tubes is provided by an interconnecting member or sectional which includes at least one gingivally-occlusally extending post for insertion into the associated at least one gingivally-occlusally extending tube on the patient's tooth. The sectional further includes a mesially extending segment disposed mesially of the post(s) and which is slidable within the associated hollow distal end of the lingual arch. At least one force generating member (e.g., an elastomeric member or compression spring) may then be disposed between two fixed locations on each side of the lingual arch such that a mesially directed force may be applied to the lingual arch and such that the lingual arch may then advance mesially relative to the sectional by a sliding-like or telescoping action. For instance, one end of the force generating member may engage effectively a fixed stop on one side of the lingual arch, while its other end may engage the tube which is fixed to the tooth. Alternatively, the mesial ends of the sectional may be hollow to slidably receive the distal ends of the lingual arch.

In yet another variation, a lingual arch (e.g., formed by a radius of less than about 0.700 inches) includes an arcuately-shaped mesial section and first and second distal sections extending from opposite ends of the mesial section. The mesial section has a diameter which is less than that of the first and second distal sections and/or is formed from a material which allows the mesial section to be deflected occlusally relative to the first and second distal sections. This again facilitates installation of the two distal ends of the lingual arch into horizontal, lingual tubes which are attached to the patient's teeth, typically via an orthodontic band.

An interconnection means of mounting assemblies can provide selective antero-posterior positioning and preferably includes a dual connection member having a first mating portion for slidable mating engagement with one of the extending portions of the connection means, and a second mating portion, oriented transversely to said first mating portion, for mating engagement with a complimentary member inter-connected to the tooth attachment means. In this regard, it is preferred that such complimentary member comprise a female means (e.g., one or more vertical tubes) fixedly connected to the tooth attachment means (e.g., a band), and that the second mating portion of the dual connection member include a male means (e.g., one or more vertical posts) for easy vertical insertion into the female means of the complimentary member. The first mating portion of the dual connection member may comprise a female means (e.g., a horizontal tube) for slidably receiving one of the extending portions of the connection means. Alternatively, the first mating portion may comprise a male means (e.g., a horizontal wire end section) for slidable positioning within a female tubular end of the connection means.

Preferably, the above-described connection member and complementary member of the interconnection means are lingually disposed for interconnection with a first extending portion of the connection means. In this regard, the interconnection means of each mounting assembly that provides selective antero-posterior positioning may also comprise a buccally disposed member for slidably engaging the second extending portion of the connection means. Preferably, the second engaging portion also extends longitudinally from the orthodontic component (e.g., rearwardly) and the buccally disposed member horizontally and slidably engages the second portion. As will be appreciated then, the above-described mounting assembly most preferably provides both lingual/buccal support and selective slidable, antero-posterior positioning for an orthodontic component relative to a given tooth or other reference position.

It has been recognized that a dual connection member and tooth attachment means having a lingually disposed complementary member (as described above) can be readily mounted on each side of the mandible so as to slidably receive an active lingual arch device there-between. In this regard, for example, it has been discovered that each end of a lingual archwire can be slidably received by a horizontal tube (e.g., each being interconnected to a corresponding dual connection member as described above) with a resilient sheath positioned on the archwire being compressed and retained between the two dual connection members. In such an arrangement, the mounting assembly facilitates mounting and allows the lingual archwire to slidably pass through the dual connection members as mandible growth is augmented in response to the expansion force applied to the lingual aspect of the lower teeth by the resilient sheath.

One embodiment of a ligature assembly includes a hollow stop tube (e.g., a hollow, generally cylindrical structure) with a hook attached thereto. An inner sleeve (e.g., a hollow, generally cylindrical structure) is disposed within at least part of the stop tube, extends out from at least the end of the stop tube which projects toward the connector, and is attached to the stop tube. A lingual arch is inserted through the stop tube and the inner sleeve and extends out the distal end of the inner sleeve. Prior to installing the end of the lingual arch in the above-described connector, a portion of the lingual arch disposed distally of the distal end of the inner sleeve may be crimped or otherwise deformed such that it will not be able to slide back through the inner sleeve. This deformation of the lingual arch limits the amount which the lingual arch will be able to move mesially relative to the inner sleeve. An alternative to the foregoing is to replace the inner sleeve with an outer sleeve which would be at least partially disposed over the stop tube, which would extend from at least one end of the stop tube and thereby be disposable over the distal end of the third segment of the corresponding connector, and which would include a hook.

One ligature assembly will typically be installed on each of the two ends of the lingual arch. The two distal ends of the lingual arch may then be inserted into the hollow tubes on the mesial ends of the third segments of two of the above-described connectors (one being installed on each side of the patient's arch undergoing treatment). The inner sleeve will also be inserted into the corresponding hollow tube of the third segment of the connector and the distal end of the stop tube will typically abut the mesial end of the hollow tube of the corresponding third segment of the connector. A ligature may then be attached to the hook on the stop tube and attached at a second distal location (e.g., on a hook associated with the corresponding connector). Although the ligature applies a ligating force to the stop tube and keeps it engaged with the mesial end of the hollow tube of the associated third segment of the connector, it provides no resistance to mesial movement of the lingual arch relative to the hollow tube of the third segment of the connector, the inner sleeve of the ligature assembly, or the stop tube of the ligature assembly until the crimped wire section of the lingual arch abuts the distal end of the inner sleeve. This could be preselected to occur at an incremental point in the lingual arch development or upon some dislodgement of the lingual arch from the patient's dentition. In either case, the ligature would then resist further mesial movement of the lingual arch.

Another type of ligature assembly which may be used with the above-described connector during lingual arch development is a hollow, typically cylindrical sectional which is slidably insertable into the hollow tube of the third segment of the connector. One of these sectionals would be installed on each end of the lingual arch and would be fixedly attached to the lingual arch (e.g., by placing bends in the two free end portions of the lingual arch which would then be fixably retained within the interior of the associated sectional by a binding-like engagement with the sectional). A hook or other appropriate mounting is attached to the sectional, and preferably another hook is attached to the third segment of the connector. Installation of this type of ligature assembly for the above-described type of lingual arch development would then further entail disposing the force-generating member, which is used to affect mesial advancement of the lingual arch, over the sectional and distally of the hook and inserting the sectional into the hollow tube portion of the third segment of the associated connector such that the forece-generating member would be retained between the connector (e.g., the hook on the third segment) and the hook on the sectional. An appropriate ligature may then be tied or otherwise attached to the hook on the third segment and also the hook on the sectional.

If there is no slack in the ligature in this last-described ligature assembly, it will immediately oppose mesial advancement of the lingual arch. However, this may actually be advantageous in some cases. For instance, the ligature may be used to reduce the magnitude of the generally mesially-directed forces being applied to the lingual arch by the force-generating member(s) (e.g., if the force-generating member applies larger than desired mesially-directed forces to the lingual arch when initially "loaded", the ligature assembly may be used to reduce the magnitude of the generally mesially-directed forces to a more desired level). Other desirable effects may be achieved with this ligature assembly. For instance, the ligature may be wrapped around the third segment and/or the sectional which will apply a torquing force to at least the tooth on which the connector is attached. When the lingual arch is also used for arch expansion, wrapping the ligature in this manner will allow the root of the tooth to also be moved transversely away from the patient's midline as a result of the torquing force generated by the wrapped ligature.

Other similar applications and extensions of the disclosed mounting assembly are possible. In this regard, it should also be noted that the assembly described hereinabove may be supplemented by plural additional components such as force generating devices, connectors, bands, archwires, tubes (e.g., horizontal, angulated or vertical), posts, etc. interconnected in various configurations to create and accommodate various orthodontic appliances and components.

Referring to the drawings, one embodiment of a lingual arch developer orthodontic assembly which accommodates the use of these types of treatment forces is illustrated in FIGS. 7A–D. The lingual arch developer 112 includes a generally U-shaped lingual arch 158 having a mesial section 114 and first and second distal sections 118, 122, respectively, which are fixedly interconnected with the mesial section 114. The mesial section 114 is generally arcuately shaped, the arcuate extent of which will typically be no greater than that defined by a radius of about 0.700 inches (although the mesial section 114 need not be defined by a single radius, the maximum radius which may be positioned within the mesial section 114 is about 0.700 inches). The mesial section 114 has a diameter of about 0.020 inches whereas each of the distal sections 118, 122 have a diameter of about 0.040 inches. That is, the first and second distal sections 118, 122, respectively, are more robust than the mesial section 114 which may be desirable for molar control (e.g., to provide resistance for tipping and/or rotation of these molars, while allowing for torquing of these molars via a labial archwire). When installed, the mesial section 114, as well as the first and second distal sections 118, 122, respectively, are disposed substantially parallel to the occlusal plane but gingivally disposed (e.g., at the gingival level of the teeth 102).

The lingual arch 158 is slidably interconnected with typically two of the orthodontic patient's teeth 102 in order to allow the lingual arch 158 to advance mesially during orthodontic treatment, and thus to mesially advance part of the patient's arch 101. In this regard, the lingual arch developer 112 further includes two horizontal tubes 132 each having a mesio-distally aperture or hole extending there-through. These tubes 132 may be fixedly interconnected with a band 134 (e.g., soldered), which is then typically attached to the patient's first molars 106 such that the tubes 132 are lingually disposed on the patient's first molars (e.g., FIG. 7C). The two distal ends 126 of the lingual arch 158 are inserted into these tubes 132 such that the first and second distal sections 118, 122, respectively, are slidably received within the tubes 132.

The lingual arch developer 112 provides for mesial movement of the lingual arch 158 during treatment in order to achieve, for instance, increased arch length for the orthodontic patient and/or to provide for desired spacings between the teeth 102 or diastamas. This movement is affected by positioning at least one force generating member 138 between the lingual arch 158 and at least one anchor location on the patient. More specifically and in the illustrated embodiment, each force generating member 138 is disposed between two "fixed points". One of these "fixed points" is on the lingual arch 158 and the other fixed point is interconnected with the anchor teeth. In the illustrated embodiment, a first force generating member 138a is positioned on the left side 146 of the lingual arch 158 between a left helical winding 154a and the left tube 132a, and a second force generating member 138b is positioned on the right side 152 of the lingual arch 158 between a right helical winding 154b and the right tube 132b. Instead of engaging the helical windings 154, a small cylindrical stop (not shown) may be disposed over each of the first and second distal sections 118, 122, may engage the associated helical winding 154, and may be engaged by the associated force generating member 138.

Appropriate force generating members 138 include devices such as compression springs (shown and e.g., helical) and axially compressible elastomers or tubing (e.g., generally tubular or cylindrical tubing which may be axially compressed, see FIGS. 1–6). In this case, when the lingual arch developer 112 is installed the force generating members 138 are under compression to generate activating forces which are generally mesially-directed on the lingual arch 158. Specifically, the force generating members 138 exert a generally mesially-directed force on the two sides 146, 152 of the lingual arch 152, and when the lingual arch 158 begins to mesially advance via the slidable interconnection with the tubes 132, part of the patient's arch 101, specifically the four anterior teeth, also begins to mesially advance. The cuspids and bicuspids will also move buccally (e.g., arch expansion) by this mesial movement of the lingual arch 158.

Figure 7A:
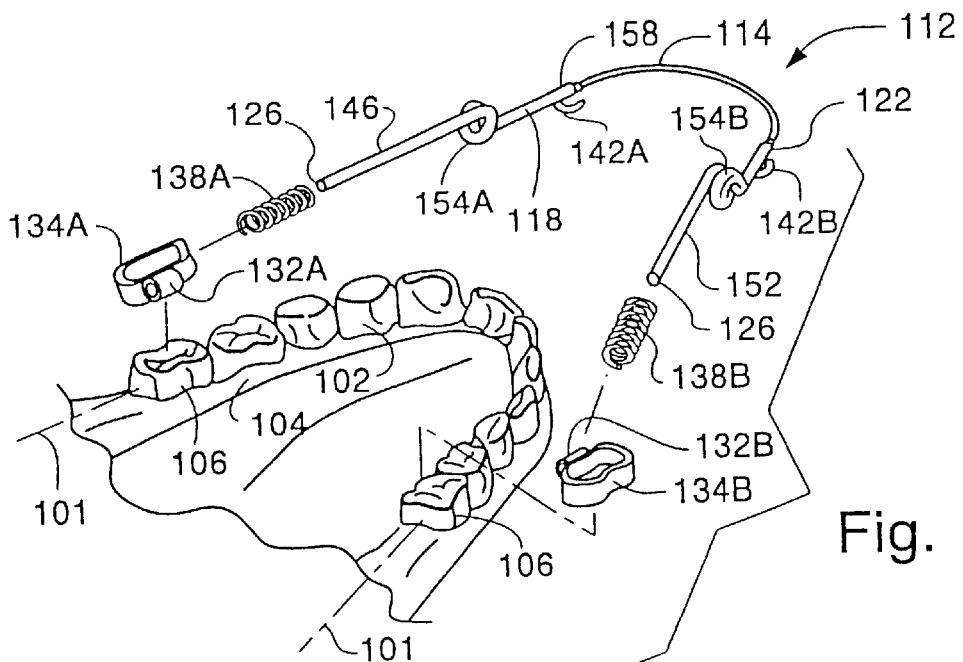
FIG. 7A is a perspective view of one embodiment of a lingual arch developer orthodontic assembly in relation to an orthodontic patient.
Figure 7B:
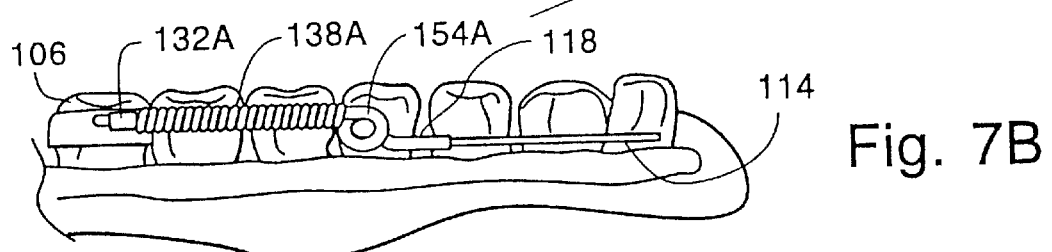
FIG. 7B is a side view of the assembly of FIG. 7A in the installed position.
Figure 7C:
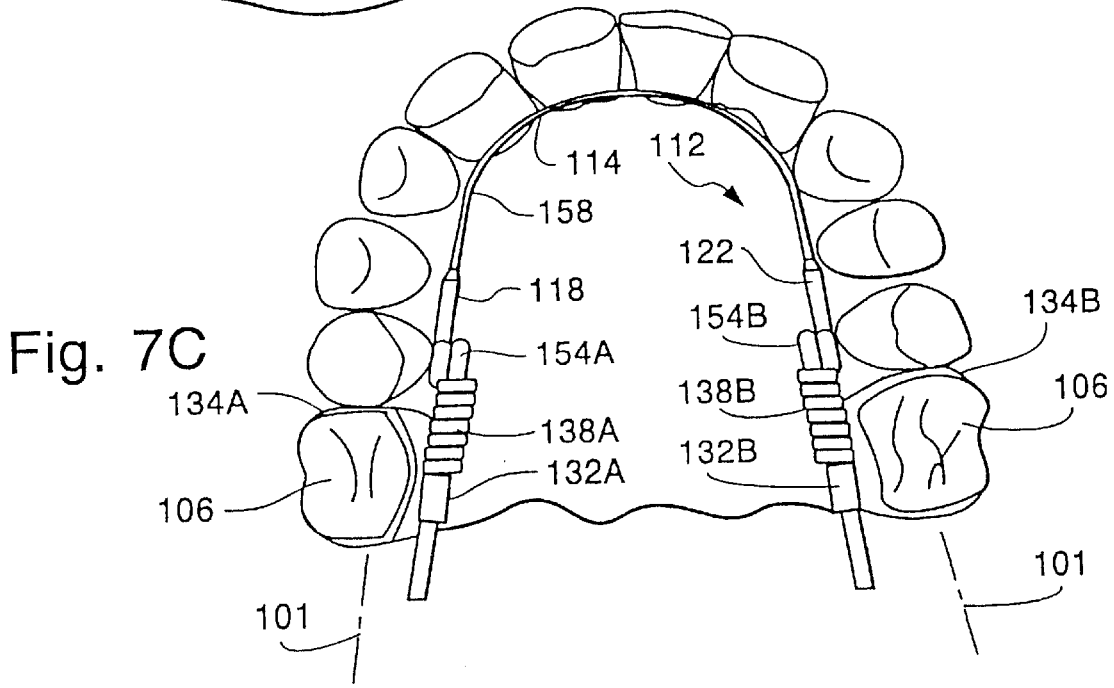
FIG. 7C is a top view of the assembly of FIG. 7A in the installed position.
Figure 7D:
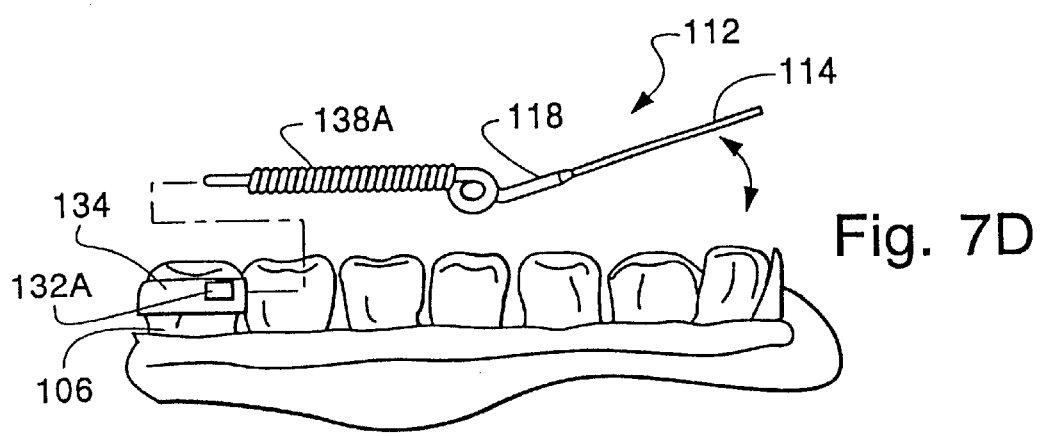
FIG. 7D is a side view of the assembly of FIG. 7A which illustrates the installation of the assembly on the patient.

In order to assist in the installation of the lingual arch 158 into the lingually disposed horizontal tubes 132, at least one, and preferably at least two helical windings 154 are incorporated into the lingual extent of the lingual arch 158. The helical windings 154 are thus disposed in sections of the lingual arch 158 which are substantially parallel to the occlusal plane but gingivally disposed (e.g., at the gingival level of the teeth 102). In the illustrated embodiment, one helical winding 154a is provided on the left side 146 of the lingual arch 158 and one helical winding 154b is provided on the right side 152 of the lingual arch 158 at substantially the same location mesio-distally. The helical windings 154 allow the mesial section 114 of the lingual arch 158 to pivot in an occlusal direction relative to the first and second distal sections 118, 122, respectively, in a predetermined manner and as illustrated in FIG. 7D. In the illustrated embodiment, the helical windings 154 extend or spiral in a downwardly direction. This offers a number of advantages. For instance, when the mesial section 114 of the lingual arch 158 is pivoted in an occlusal direction relative to the first and second distal sections, 118, 122, respectively, the inside diameter of the helical windings 154 increases. Less resistance may be encountered when pivoting the lingual arch 158 in this manner than if the helical windings 154 were generally upwardly extending (not shown). Moreover, the downwardly extending helical windings 154 also provide a way to position the portion of the lingual arch 158 disposed mesially of the helical windings 154 at a more gingival location that the portion of the lingual arch 158 disposed distally of the helical windings 154 as illustrated in FIG. 7B. Disposing the lingual arch 158 gingivally is desired for orthodontic treatment such that the lingual arch is disposed closer to the tooth's centroid.

The size, location, and/or orientation of the helical windings 154 may be selected to facilitate the generation of orthodontic treatment forces in addition to those generated by the force generating members 138. For instance, the helical windings 154 may be disposed to apply rotational forces to the molars 106. Moreover, the helical windings 154 may be oriented to generate/augment arch expansion forces. Nonetheless, the helical windings 154 are disposed in sections of the lingual arch 158 which are substantially parallel to the occlusal plane but gingivally disposed (e.g., at the gingival level of the teeth 102).

The lingual arch 158 slidably advances relative to the tubes 132 in a mesial direction as orthodontic treatment progresses. In order to reduce the potential for the lingual arch 158 advancing too far such that it becomes disengaged from the tubes 132, at least one ligature (e.g., metal or elastic and not shown), may be disposed between at least one of the hooks 142 and the associated tube 132 (e.g., on the same side) and/or a hook (not shown) attached to the band 134. A stout elastic could be utilized which, during the initial part of orthodontic treatment with the lingual arch developer 112, would not be under tension. After treatment had progressed a certain degree (e.g., after a certain degree of mesial advancement of the lingual arch 158 has been achieved by the lingual arch 158 advancing relative to the tubes 132), the elastic would come under tension to retain the lingual arch 158 at least partially within the tubes 132. This not only accomplishes a desired safety objective of reducing the potential for the lingual arch 158 becoming dislodged, but it also allows for treatment to progress incrementally. A metal ligature could also be utilized which would have some "slack" at the start of treatment, but would become taut before the lingual arch 158 became dislodged from the tubes 132, all to provide the same objectives as the elastic ligature. In the case of a metal ligature, it could be disposed within the associated force generating member 138 (e.g., disposed inside of a spring).

Figure 8C:
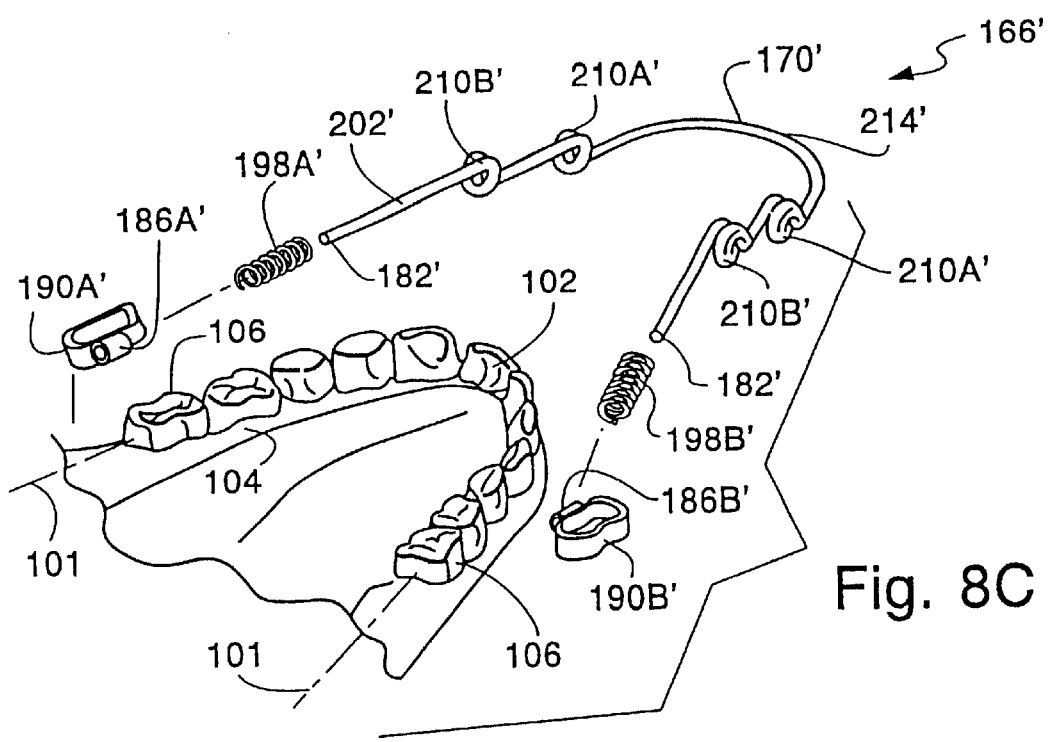
FIG. 8C is a perspective view of the assembly of FIG. 8A with an additional pair of helices.
Figure 8D:
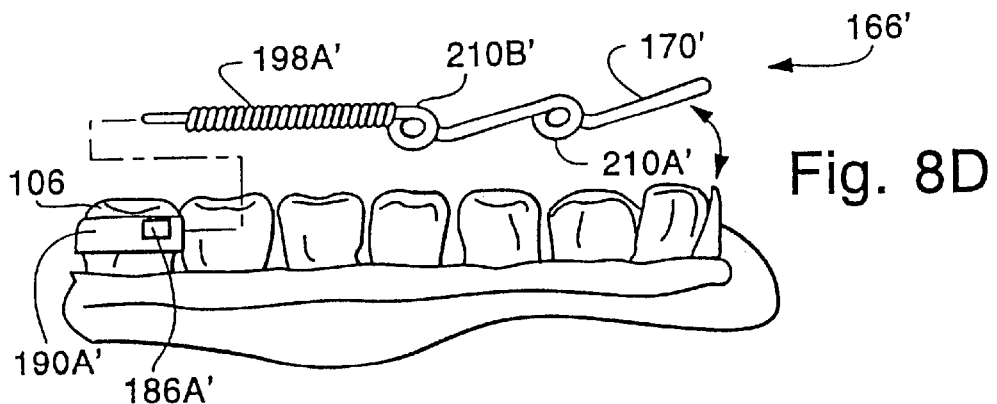
FIG. 8D is a side view of the assembly of FIG. 8C.
Figure 8A:
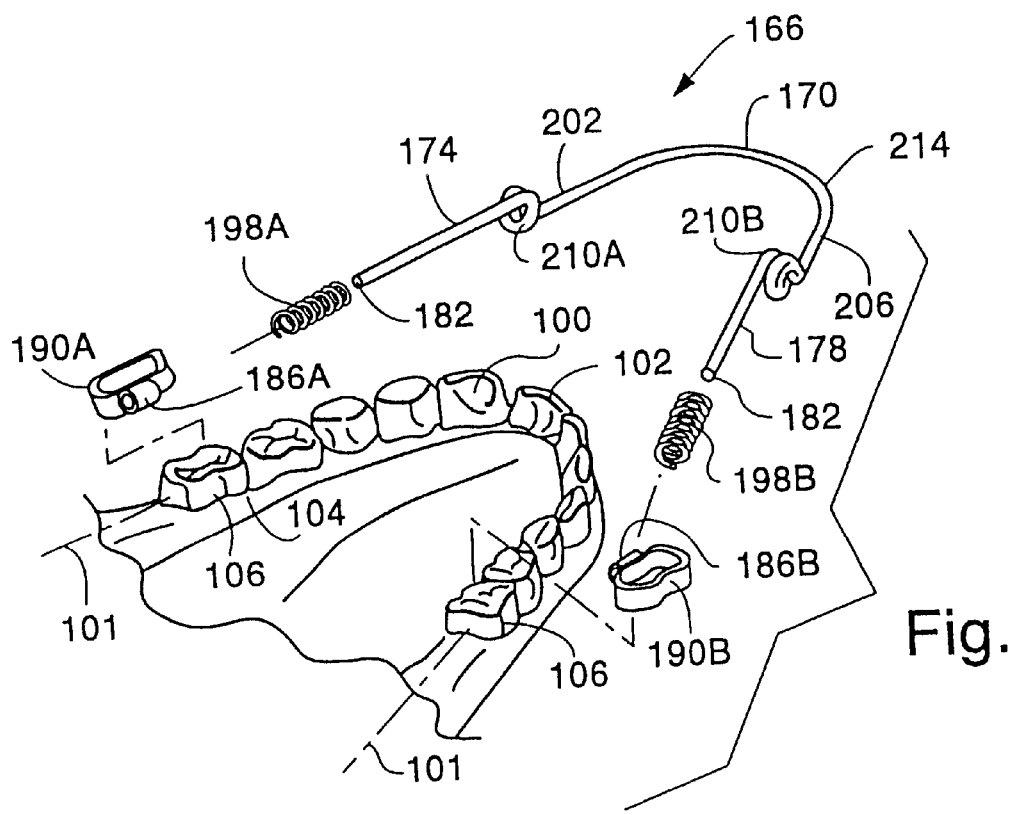
FIG. 8A is a perspective view of another embodiment of a lingual arch developer orthodontic assembly in relation to an orthodontic patient.
Figure 8B:
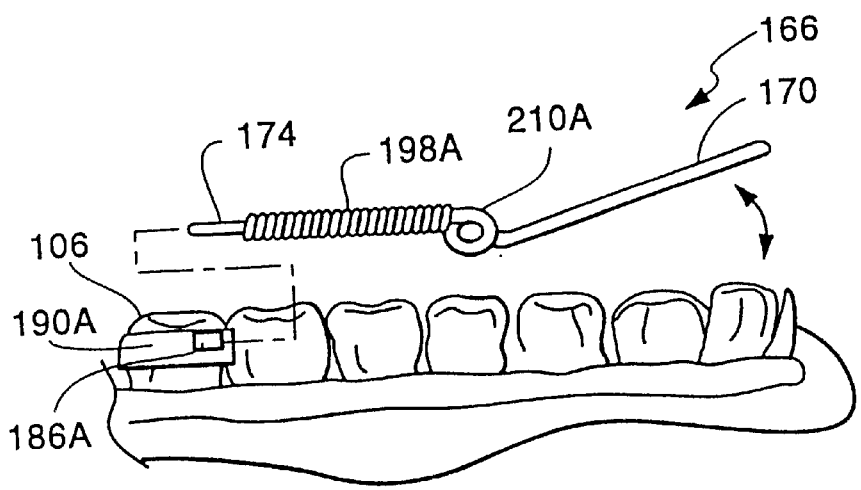
FIG. 8B is a side view of the assembly of FIG. 8A which illustrates the installation of the assembly on the patient.

Another embodiment of a lingual arch developer orthodontic assembly which accommodates the use of the generally mesially directed treatment forces is illustrated in FIGS. 8A–B. The lingual arch developer 166 includes a generally U-shaped lingual arch 214 having a mesial section 170 and first and second distal sections 174, 178, respectively, integrally formed with the mesial section 170. The mesial section 170 is generally arcuately shaped, the arcuate extent of which will typically be no greater than that defined by a radius of about 0.700 inches (e.g., although the mesial section 170 need not be defined by a single radius, the maximum radius which may be positioned within the mesial section 170 is about 0.700 inches). In this embodiment, the lingual arch 214 is of constant diameter with regard to the wire which forms the same (e.g., the diameter of the mesial section 170 in cross section is equal to the diameters of each of the first and second distal sections 174, 178 in cross section). When installed, the mesial section 170, as well as the first and second distal sections 174, 178, respectively, are disposed substantially parallel to the occlusal plane but gingivally disposed (e.g., at the gingival level of the teeth 102).

The lingual arch 214 is slidably interconnected with typically two of the orthodontic patient's teeth 102 in order to allow the lingual arch 214 to advance mesially during orthodontic treatment, and thus to mesially advance the patient's arch 101 in the above-noted manner. In this regard, the lingual arch developer 166 further includes two horizontal tubes 186 each having a mesio-distally aperture or hole extending there-through. These tubes 186 may be fixedly interconnected with a band 190 (e.g., soldered), which is then typically attached to the first molars 106 such that the tubes 186 are lingually disposed on the patient's teeth 102. The two distal ends 182 of the lingual arch 214 may therefore be inserted into these tubes 186 such that the first and second distal sections 174, 178, respectively, are slidably received within the tubes 186.

The lingual arch developer 166 provides for mesial movement of the lingual arch 214 during treatment in order to achieve, for instance, increased arch length for the orthodontic patient and/or to provide for desired spacings between the teeth 102. This movement is affected by positioning at least one force generating member 198 between the lingual arch 214 and at least one anchor location on the patient. More specifically and in the illustrated embodiment, each force generating member 198 is disposed between two fixed points. One of these fixed points is on the lingual arch 214, such as against one of the helical windings 210 or a cylindrical member disposed about the lingual arch 214 and which abuts the associated helical winding 210 (not shown), and the other fixed point is interconnected with the patient's teeth 102. In the illustrated embodiment, a first force generating member 198a is positioned on the left side 202 of the lingual arch 214 between the left helical winding 210a and the left tube 186a, and a second force generating member 198b is positioned on the right side 206 of the lingual arch 214 between the right helical winding 210b and the right tube 186b.

Appropriate force generating members 198 include devices such as compression springs (shown and e.g., helical) and axially compressible elastomers (e.g. generally tubular or cylindrical tubing which may be axially compressed, see FIGS. 1–6). In this case, when the lingual arch developer 166 is installed the force generating members 198 are under compression to generate activating forces which are generally mesially-directed. That is, the force generating members 198 exert a generally mesially-directed force on the two sides 202, 206 of the lingual arch 214, and when the lingual arch 214 mesially advances via the slidable interconnection with the tubes 186, the patient's arch 101 advances in the above-noted manner.

In order to assist in the installation of the lingual arch 214 into the lingually disposed horizontal tubes 186, at least one and preferably at least two helical windings 210 are incorporated into the lingual extent of the lingual arch 214. The helical windings 210 are thus disposed in sections of the lingual arch 214 which are substantially parallel to the occlusal plane but gingivally disposed (e.g., at the gingival level of the teeth 102). In the illustrated embodiment, one helical winding 210a is provided on the left side 202 of the lingual arch 214 and one helical winding 210b is provided on the right side 206 of the lingual arch 214 at substantially the same location mesio-distally. The helical windings 210 allow the mesial section 170 of the lingual arch 214 to pivot in an occlusal direction relative to the first and second distal sections 174, 178, respectively, in a predetermined manner and as illustrated in FIG. 8B. In the illustrated embodiment, the helical windings 210 extend in a downwardly direction to provide the above-noted advantages.

The size, location, and/or orientation of the helical windings 210 may also be selected to facilitate the generation of orthodontic treatment forces in addition to those generated by the force generating members. For instance, the helical windings 210 may be disposed to apply rotational forces to the first molars 106. Moreover, the helical windings 210 may be oriented to generate/augment arch expansion forces. Nonetheless, the helical windings 210 are disposed in sections of the lingual arch 214 which are substantially parallel to the occlusal plane but gingivally disposed (e.g., at the gingival level of the teeth 102).

Four helical windings 210' may be incorporated into the lingual arch 214' as well and as illustrated in FIGS. 8C–D. In this case, two helical windings 210' could be disposed on the left side 202' of the lingual arch 214' and two helical windings 210' could be disposed on the right side 206' of the lingual arch 214'. In this case, two of the helical windings 210a' could be disposed at one mesio-distal location on opposite sides of the lingual arch 214', and the other two of the helical windings 210b' could be more distally disposed at the same mesio-distal position on opposite sides of the lingual arch 214'. This could allow the mesially located pair of helical windings 210a' to be oriented so as to store arch expansion forces and the distally located pair of helical windings 210b' to be oriented to store rotationally directed forces (e.g., for rotating the first molars 106 when the tubes 190' are installed thereon).

Figure 9:
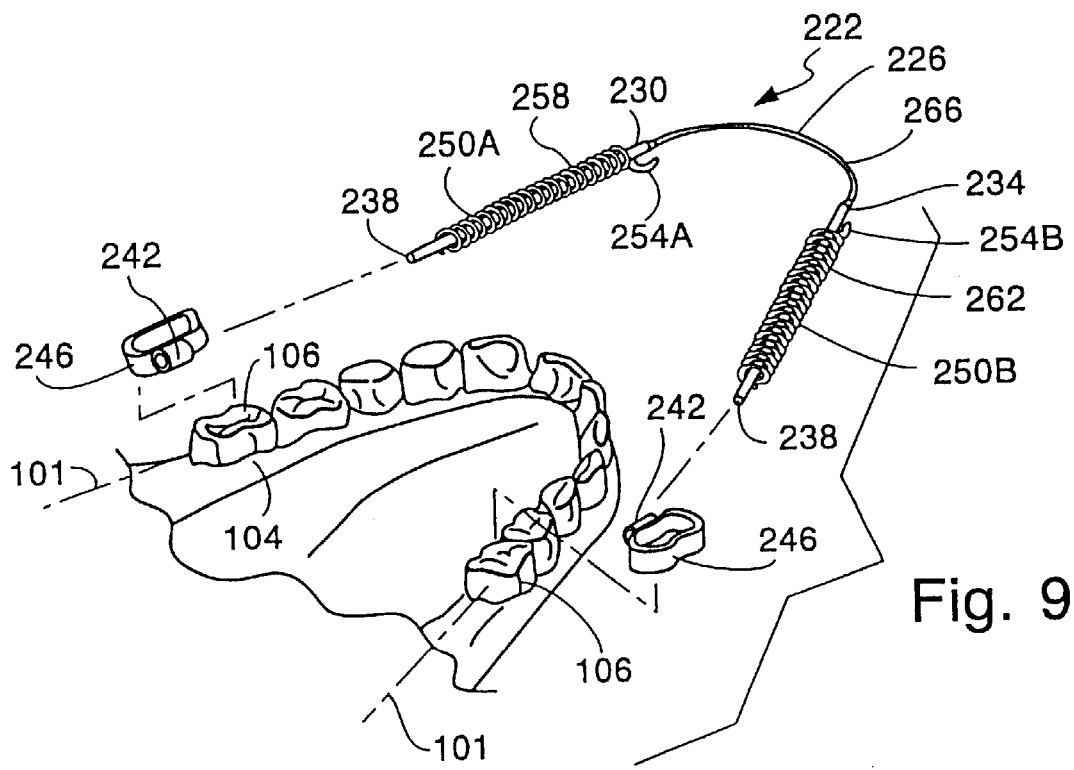
FIG. 9 is a perspective view of another embodiment of a lingual arch developer orthodontic assembly in relation to an orthodontic patient.

Another lingual arch developer which may be used for arch development by the application of generally mesially-directed forces to the lingual of a patient's teeth is illustrated in FIG. 9. The lingual arch developer 222 includes a generally U-shaped lingual arch 266 having a mesial section 226 and first and second distal sections 230, 234, respectively, which are fixedly interconnected with the mesial section 226. The mesial section 226 is generally arcuately shaped, the arcuate extent of which will typically be no greater than that defined by a radius of about 0.700 inches (although the mesial section 226 need not be defined by a single radius, the maximum radius which may be positioned within the mesial section is about 0.700 inches). The mesial section 226 has a diameter of about 0.020 inches whereas each of the distal sections 230, 234 have a diameter of about 0.040 inches. That is, the first and second distal sections 230, 234, respectively, are more robust than the mesial section 226 which may be desirable for certain types of orthodontic treatment as noted above. When installed, the mesial section 226, as well as the first and second distal sections 230, 234, respectively, are disposed substantially parallel to the occlusal plane but gingivally disposed (e.g., at the gingival level of the teeth 102).

The lingual arch 266 is slidably interconnected with typically two of the orthodontic patient's teeth 102 in order to allow the lingual arch 266 to advance mesially during orthodontic treatment, and thus to advance the patient's arch 101 in the above-noted manner. In this regard, the lingual arch developer 222 further includes two horizontal tubes 242 each having a mesio-distally aperture or hole extending there-through. These tubes 242 may be fixedly interconnected with a band 246, which is then typically attached to the patient's first molars 106 such that the tubes 242 are lingually disposed on the patient's first molars 106. The two distal ends 238 of the lingual arch 266 may therefore be inserted into these tubes 242 such that the first and second distal sections 230, 234, respectively, are slidably received within the tubes 242.

The lingual arch developer 222 provides for mesial movement of the lingual arch 266 during treatment in order to achieve, for instance, increased arch length for the orthodontic patient and/or to provide for desired spacings between the teeth 102. This movement is affected by positioning at least one force generating member 250 between the lingual arch 266 and at least one anchor location. More specifically and in the illustrated embodiment, each force generating member 250 is disposed between two fixed points. One of these fixed points is on the lingual arch 266, such as a hook 254 which also may be used as a safety feature as discussed below, and the other fixed point is interconnected with the patient's anchor teeth. In the illustrated embodiment, a first force generating member 250a is positioned on the left side 258 of the lingual arch 266 between the left hook 254a and the left tube 242a, and a second force generating member 250b is positioned on the right side 262 of the lingual arch 266 between the right hook 254b and the right tube 242b.

Appropriate force generating members 250 include devices such as compression springs (shown and e.g., helical) and axially compressible elastomers (e.g., generally tubular or cylindrical tubing which may be axially compressed). In this case, when the lingual arch developer 222 is installed the force generating members 250 are under compression to generate activating forces which are generally mesially-directed. That is, the force generating members 250 exert a generally mesially-directed force on the two sides 258, 262 of the lingual arch 266, and when the lingual arch 266 advances mesially via the slidable interconnection with the tubes 242, the patient's arch 101 advances in the above-noted manner.

In order to assist in the installation of the lingual arch 266 into the horizontal tubes 242, the mesial section 226 of the lingual arch 266 may be deflected occlusally relative to the first and second distal sections 230, 234, respectively, of the lingual arch 266 since the diameter of the mesial section 226 is less than that of each of the first and second distal sections 230, 234, respectively. With the mesial section 226 deflected in this manner and with the force generating members 250 being installed over the first and second distal sections 230, 234, respectively, the distal ends 238 of the lingual arch 266 may be advanced within the tubes 242 a sufficient distance such that the mesial section 226 of the lingual arch 266 may be disposed inside of the patient's arch 101.

The lingual arch 266 slidably advances relative to the tubes 242 in a mesial direction as orthodontic treatment progresses. In order to reduce the potential for the lingual arch 266 advancing too far such that it becomes disengaged from the tubes 242, at least one ligature (e.g., metal or elastic and not shown), may be disposed between at least one of the hooks 254 and the associated tube 242 (e.g., on the same side) or a hook (not shown) also positioned on the tube 242 or the band 246. A stout elastic could be utilized which, during the initial part of orthodontic treatment with the lingual arch developer 222, would not be under tension. After treatment had progressed a certain degree (e.g., after a certain degree of mesial advancement of the lingual arch 266 has been achieved by the arch 266 advancing relative to the tubes 242), the elastic would come under tension to retain the lingual arch 266 in the tubes 242. This not only accomplishes a desired safety objective of reducing the potential for the arch 266 becoming dislodged, but it also allows for treatment to progress incrementally. A metal ligature could also be utilized which would have some "slack" at the start of treatment, but would become taut before the arch 266 became dislodged from the tubes 242, all to provide the same objectives as the elastic. In the case of a metal ligature, it could be disposed within the associated force generating member 250.

Figure 10A:
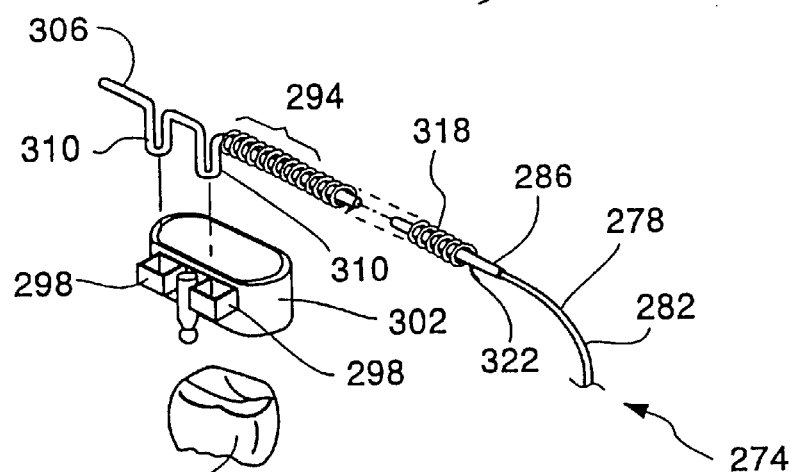
FIG. 10A is a partial, exploded, perspective view of another embodiment of a lingual arch developer orthodontic assembly.
Figure 10C:
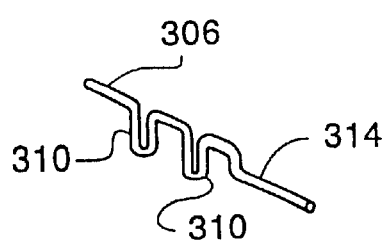
FIG. 10C is a perspective view of a connector used with the lingual arch developer of FIG. 10A.
Figure 10B:
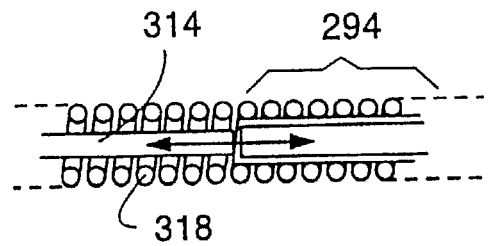
FIG. 10B is a side view of the assembly of FIG. 10A which illustrates the telescoping nature of the developer of FIG. 10A.

Another lingual arch developer which may be used for arch development by the application of forces to the lingual of a patient's teeth is illustrated in FIGS. 10A–C. The lingual arch developer 274 is an orthodontic assembly which includes a generally U-shaped lingual arch 278 having a mesial section 282, a first distal section 286, and left distal section (not shown, but the mirror image of the first distal section 286 in that it is on the opposite side of the patient's jaw). The mesial section 282 is fixedly interconnected with the first distal section 286 and the second distal section. The mesial section 282 is also generally arcuately shaped, the arcuate extent of which will typically be no greater than that defined by a radius of about 0.700 inches (although the mesial section 282 need not be defined by a single radius, the maximum radius which may be positioned within the mesial section is about 0.700 inches). The mesial section 282 has a diameter of about 0.020 inches whereas each of the distal sections have a diameter of about 0.040 inches. That is, the first distal section 286 and the second distal section (not shown), are more robust than the mesial section 282 which may be desirable for certain types of orthodontic treatment. The first distal section 286 and the second distal section are shorter than the first and second distal sections 118, 122, respectively, of the lingual arch developer 112 of FIGS. 7A–D and shorter than the first and second distal sections 230, 234, respectively, of the lingual arch developer 222 of FIG. 9, and at least the distal-most portion 294 of the first distal section 286 and the distal-most portion of the second distal section (not shown), are hollow for establishing a slidable interconnection with the patient's teeth 102 in a manner described in more detail below. When installed, the mesial section 282, as well as the first distal section 286 and the second distal section, are disposed substantially parallel to the occlusal plane but gingivally disposed (e.g., at the gingival level of the teeth 102).

The lingual arch 278 is slidably interconnected with typically two of the orthodontic patient's teeth in order to allow the lingual arch 278 to advance mesially during orthodontic treatment, and thus to mesially advance the patient's arch. In this regard, the lingual arch developer 274 further includes at least one generally occlusal-gingivally extending tube 298, and preferably two of such tubes 298, which may be fixedly interconnected with a band 302, which is then typically attached to one of the patient's first molars 106 such that the tubes 298 are lingually disposed on the patient's first molars 106. One of these bands 302 with the tube(s) 298 thereon would be positioned on the first molar 106 on one side of the patient's jaw, while another band 302 with the tube(s) 298 thereon would be positioned on the first molar on the other side of the patient's jaw.

A sectional 306 is installed in each pair of tubes 298 on the first molars 106. Each sectional 306 is preferably integrally formed (i.e., of one-piece construction) and includes two generally occlusal-gingivally extending posts 310. These posts 310 are disposed in the pair of tubes 298. Each sectional 306 also includes a mesially extending section 314 which is disposed mesially of each of the posts 310. The mesially extending section 314 is also gingivally offset as best illustrated in FIG. 10C. The mesially extending sections 314 are each sized so as to be positionable and slidable within the hollow distal-most portions 294 of the associated first distal section 286 or the second distal section of the lingual arch 278. Alternatively, the sections 314 could be hollow to slidably receive the distal sections of the lingual arch 278.

The lingual arch developer 274 provides for mesial movement of the lingual arch 278 during treatment in order to achieve, for instance, increased arch length for the orthodontic patient and/or to provide for desired spacings between the teeth. This movement is affected by positioning at least one force generating member 318 between each the lingual arch 278 and at least one anchor location on the patient. More specifically and in the illustrated embodiment, each force generating member 318 is disposed between two fixed points. One of these fixed points is on the lingual arch 278, such as a hook 322 which also may be used as a safety feature as discussed below, and the other fixed point is interconnected with the patient's anchor teeth. In the illustrated embodiment, the force generating member 318 is positioned on the left side of the lingual arch 278 between the left hook 322 and mesial left tube 298, and a second force generating member (not shown) is positioned on the right side (not shown) of the lingual arch 278 between the right hook (not shown) and the mesial right tube (not shown).

Appropriate force generating members 318 include devices such as compression springs (shown and e.g., helical) and axially compressible elastomers (e.g., generally tubular or cylindrical tubing which may be axially compressed, see FIGS. 1–6). In this case, when the lingual arch developer 274 is installed the force generating members 318 are under compression to generate activating forces which are generally mesially-directed. That is, the force generating members 318 exert a generally mesially-directed force on the two sides of the lingual arch 278, and when the lingual arch 278 mesially advances by the slidable interconnection with the patient's teeth on which the tubes 298 are disposed (i.e., by the telescoping of the lingual arch 278 relative to the two sectionals 306, specifically by the first and distal sections sliding mesially relative to the associated mesially extending section 314 of the associated sectional 306), the patient's arch advances in the above-noted manner.

As will be appreciated, the lingual arch developer 274 alleviates the need for any pivotal-like action for installation of the lingual arch 278 on the patient. Summarily, one force generating member 318 is disposed over each of the first distal section 286 and the sectional 306, specifically its mesially extending section 314, which is inserted into the distal-most portion 294 of the first distal section 286. The second distal section is similarly interconnected with its corresponding sectional. The force generating members 318 are then compressed a sufficient degree such that the lingual arch developer 274 may be dropped within the lingual arch of the orthodontic patient, with the posts 310 of each sectional 306 being inserted into their associated tubes 298.

The lingual arch 278 slidably advances relative to the tubes 298, via the telescoping of the first distal section 286 and the second distal section on the associated mesially extending section 314 of the associated sectional 306, in a mesial direction as orthodontic treatment progresses. In order to reduce the potential for the lingual arch 278 advancing too far such that it becomes disengaged from the sectional 306, at least one ligature (e.g., metal or elastic), may be disposed between at least one of the hooks 322 and the associated tube 298 and/or hook attached to the band 302 (e.g., on the same side). A stout elastic could be utilized which, during the initial part of orthodontic treatment with the lingual arch developer 274, would not be under tension. After treatment had progressed a certain degree (e.g., after a certain degree of mesial advancement of the lingual arch 278 has been achieved by the lingual arch 278 advancing relative to the tubes 298), the elastic would come under tension to retain the arch 278 on the mesially extending sections 314 of the sectionals 306. This not only accomplishes a desired safety objective of reducing the potential for the arch 278 becoming dislodged, but it also allows for treatment to progress incrementally. A metal ligature could also be utilized which would have some "slack" at the start of treatment, but would become taut before the arch 278 became dislodged from the sectionals 306, all to provide the same objectives as the elastic. In the case of a metal ligature, it could be disposed within the associated force generating member.

Another embodiment of a device for interconnecting an orthodontic appliance with a patient's tooth, including any of the above-described lingual arch developers, is illustrated in FIGS. 11–12. The connector 326 provides an interface between a band (not shown) attached to a patent's tooth (e.g., a first molar) and an orthodontic appliance, such as a lingual arch of a lingual arch developer. Hereafter, the connector will be described for lingual applications, although it will be appreciated that the connector may have some applications on the buccal.

The connector 326 includes two generally occlusal-gingivally extending posts 330 with the mesial post 330a extending more gingivally than the distal post 330b. Although shown as being in the occlusal-gingival reference plane 346, the posts may be lingually tipped to a small degree (e.g., about 10°). These posts 330 are slidably insertable into a pair of corresponding, generally occlusal-gingivally extending tubes (not shown) attached to the patient's teeth via a band (not shown) (e.g., see band 302 and tubes 298 in FIG. 10). Although these posts 330 could be separately formed, in the illustrated embodiment they are integrally formed.

A first segment 334 is generally mesio-distally extending and is interconnected with one or more of the posts 330. Although the first segment 334 and posts 330 could be integrally formed, in the illustrated embodiment the posts 330 are integrally formed and separately attached to the first segment 334 (e.g., laser welding, brazing). The first segment 334 extends distally of at least the mesial post 330a, and in the illustrated embodiment also extends distally of the distal post 33b.

The connector 326 further includes a second segment 338 which is interconnected with the first segment 334. The second segment 338 is generally semi-circular. Therefore, the second segment 338 initially extends gingivally and distally from the first segment 334 along an arcuate path. At the mid point of the second segment 338, the second segment 338 then extends generally gingivally and mesially along an arcuate path from this midpoint. Although the second segment 338 could be separately attached to the first segment 334, preferably the first segment 334 and second segment 338 are integrally formed.

A third segment 342 is interconnected with the second segment 338 and extends generally mesially from the second segment 338. The entire third segment 342 is a generally cylindrical, hollow tube in the illustrated embodiment, although only the mesial-most portion of an appropriate length need be of this type of construction. In one embodiment, the tube portion of the third segment 342 has an inner diameter ranging from about 0.025 inches (0.635 mm) to about 0.060 inches (1.524 mm). The second segment 338 may actually extend within the distal end of the third segment 342 a short distance and be appropriately secured thereto (e.g., laser welding, brazing). In one embodiment, the mesial end of the second segment 338 extends about 3 mm into the distal end of the third segment 342.

As is evident by review of FIG. 11, the third segment 342 is gingivally disposed relative to the first segment 334. The third segment 342 may slidably interface with an end of a force generating device, a lingual arch and other orthodontic appliances. For instance and in the illustrated embodiment, an end of a lingual arch may be slidably received in the mesial end of the third segment 342. The connector 326 is also advantageous in that the third segment 342 may be of a length which provides for enhanced stability of the lingual arch or other orthodontic appliance therewithin and/or for extended mesial movement of the lingual arch relative to the third segment 342 without the lingual arch becoming disengaged from the third segment 342. In one embodiment, the length of the tube portion of the third segment 342 available for interfacing with the lingual arch or another orthodontic appliance may range from about 7 mm to about 16 mm, and is preferably about 12 mm.

In the illustrated embodiment and as best illustrated in FIG. 12, the third segment 342 is also actually lingually offset in relation to the first segment 334 (i.e., the third segment 342 is disposed closer to the patient's tongue than the first segment 334). Advantages associated with the lingual offset include rotational considerations and it also facilitates the installation of the connector 326. Lingual offsetting of the third segment 342 may be provided by having the second segment 338 generally contained within a plane which is disposed at an angle relative to an occlusal-gingivally extending reference plane 346. In one embodiment, this first angle 344 ranges from about 20° to about 55°, and in the illustrated embodiment is actually about 45°. As such, the third segment 342 need not be moved relative to the first segment 334 in order to install the posts 330 into the generally vertically extending tubes on the orthodontic band.

The connector 326 may also include a hook 350. Generally, the hook 350 is interconnected with the first segment 334 and extends generally mesially from the first segment 334. Although the hook 350 could be separately attached to the mesial end of the first segment 334, preferably the hook 350 is integrally formed with the first segment 334. In the illustrated embodiment, the hook 350 also extends gingivally and lingually from the first segment 334 as illustrated in FIG. 12. The opening to the hook 350 projects generally distally such that a ligature (not shown) may interface with the hook 350 and a location disposed mesially thereof.

A variation of the connector 326 is illustrated in FIGS. 13–14. Portions of the connector 326$^i$ of FIGS. 13–14 which at least generally correspond to portions of the connector 326 of FIGS. 11–12 are similarly numbered, followed by a superscripted "i" designation. The main difference between the connector 326$^i$ of FIGS. 13–14 and the connector 326 of FIGS. 11–12 is that the hook 350 of connector 326 has been replaced with a generally mesio-distally extending, generally horizontally disposed tube 360. The tube 360 is occlusally disposed relative to the third segment 342$^i$ of the connector 326$^i$. The tube 360 is also typically generally cylindrical and hollow, and will typically have an inner diameter ranging from about 0.025 inches (0.635 mm) to about 0.060 inches (1.524 mm) and a length for interfacing with an orthodontic appliance ranging from about 7 mm to about 16 mm. In the illustrated embodiment, the tube 360 extends mesially beyond the mesial end of the third segment 342$^i$. The horizontal tube 360, as well as the horizontal tube 342$^i$, may be used to provide an interface with a variety of types of orthodontic appliances, such as a spring-driven palatal expander. Therefore, the connector 326$^i$ need not be limited to use with lingual arch development, but instead may be used for other applications as well. Moreover, the horizontal tube 360 may interface with the posts 330$^i$ without a need for the third segment 342$^i$ (not shown). That is, the connector 326$^i$ could be modified to include only the post(s) 330$^i$ and the horizontal tube 360 (not shown).

Another embodiment of a connector which may be utilized with each of the above-described lingual arch developers is illustrated in FIG. 15. The connector 326$^{ii}$ of FIG. 15 is generally similar to the connector 326 of FIGS. 11–12 discussed above. Portions of the connector 326$^{ii}$ of FIG. 15 which at least generally correspond to portions of the connector 326 of FIGS. 11–12 are similarly numbered, followed by a superscripted "ii" designation. One difference between the connector 326$^{ii}$ of FIG. 15 and the connector 326 of FIG. 11 is that the hook 364 in FIG. 15 does not extend gingivally down like the hook 350 of the connector 326, but is instead generally mesio-distally extending. Another difference between the connector 326 and the connector 326$^{ii}$ is that the connector 326$^{ii}$ interfaces with a ligature assembly 368 which in turn interfaces with the lingual arch developer to reduce the potential for the lingual arch developer becoming dislodged. However, the ligature assembly 368 could be used with all connectors described herein unless otherwise noted.

The ligature assembly 368 allows for the above-described types of lingual arch developers to be ligated to the connector 326$^{ii}$ without providing any significant resistance to the mesial advancement of the lingual arch for a predetermined amount of mesial advancement of the lingual arch. The ligature assembly 368 generally includes a stop tube 372 which in the illustrated embodiment is generally cylindrical and hollow. An inner sleeve 376 is disposed partially within the distal end of the stop tube 372, extends distally from the stop tube 372, and is appropriately secured to the stop tube 372 (e.g., laser welding, brazing). The outer diameter of the inner sleeve 376 is selected to be smaller than the inner diameter of the third segment 342$^{ii}$ of the connector 326$^{ii}$ such that it may be slidably received therein without sacrificing stability. In one embodiment, there is about a 0.002 inch (0.0508 mm) to about 0.004 inch (0.01016 mm) annular gap between the inner sleeve 376 and the inner diameter of the third segment 342$^{ii}$.

In order to install a lingual arch developer utilizing the ligature assembly 368, first an appropriate force generating member 396 is installed on the lingual arch 384. The distal end of a lingual arch 384 is disposed through the mesial end of the stop tube 372 to extend through the inner sleeve 376 and distally from the distal end of the inner sleeve 376 an appropriate distance. The distal end of the force generating member 396 may abut the mesial end of the stop tube 372. A crimp 388 or other deformation may be formed on a distal portion of the lingual arch 384. The lingual arch 384 may then slide into the hollow interior of the third segment 342$^{ii}$ of the connector 326$^{ii}$. The crimp 388 in the lingual arch 384 is freely, slidably received within the hollow interior of third segment 342$^{ii}$. After installing the opposite end of the lingual arch 384 on another connector 326$^{ii}$ disposed on the opposite side of the patient's mouth in this same general manner, the connectors 326$^{ii}$ may be installed in the generally vertical tubes on the respective bands in the above-described manner.

The ligature assembly 368 is disposed mesially of the connector 326$^{ii}$ such that the inner sleeve 376 extends within the hollow interior of the third segment 342 and the distal end of the stop tube 372 engages the mesial end of the third segment 342$^{ii}$. A ligature 392 (e.g., elastic, metal) may then engage the hook 364 on the connector 326$^{ii}$ and extend down into engagement with a tiehook 380 which is attached to the stop tube 372 of the ligature assembly 368. The ligature 392 may be exerting at least a distally directed force on the stop tube 372 to maintain engagement between the stop tube 372 and the third segment 342$^{ii}$ of the connector 326$^{ii}$. However, since the lingual arch 384 is slidable relative to the stop tube 372, as well as the inner sleeve 376 and the third segment 342$^{ii}$ of the connector 326$^{ii}$ and since the crimp 388 is disposed distally of the distal end of the stop tube 372, no resistance is provided to mesial movement of the lingual arch 384 relative to the connector 326$^{ii}$ at this time. Once the lingual arch 384 has advanced such that the crimp 388 engages the distal end of the inner sleeve 376, however, the ligature 392 will begin to oppose further mesial movement of the lingual arch 384. Further mesial movement of the lingual arch 384 will cause the distal end of the stop tube 372 to become displaced from the mesial end of the third segment 342$^{ii}$ of the connector 326$^{ii}$ as illustrated in FIG. 15A.

Having the ligature assembly 368 generate opposing forces to the mesial advancement of the lingual arch 384 after a certain amount of mesial advancement may be used as an indicator of an incremental advancement in the treatment of the orthodontic patient and may trigger a visit to the orthodontist. Alternatively, this resistance will assist in maintaining the interconnection between the lingual arch 384 and the third segment 342$^{ii}$ of the connector 326$^{ii}$ if the lingual arch 384 inadvertently becomes disengaged with the patient's dentition (e.g., the ligature assembly 368 provides safety enhancement features).

Figure 16:
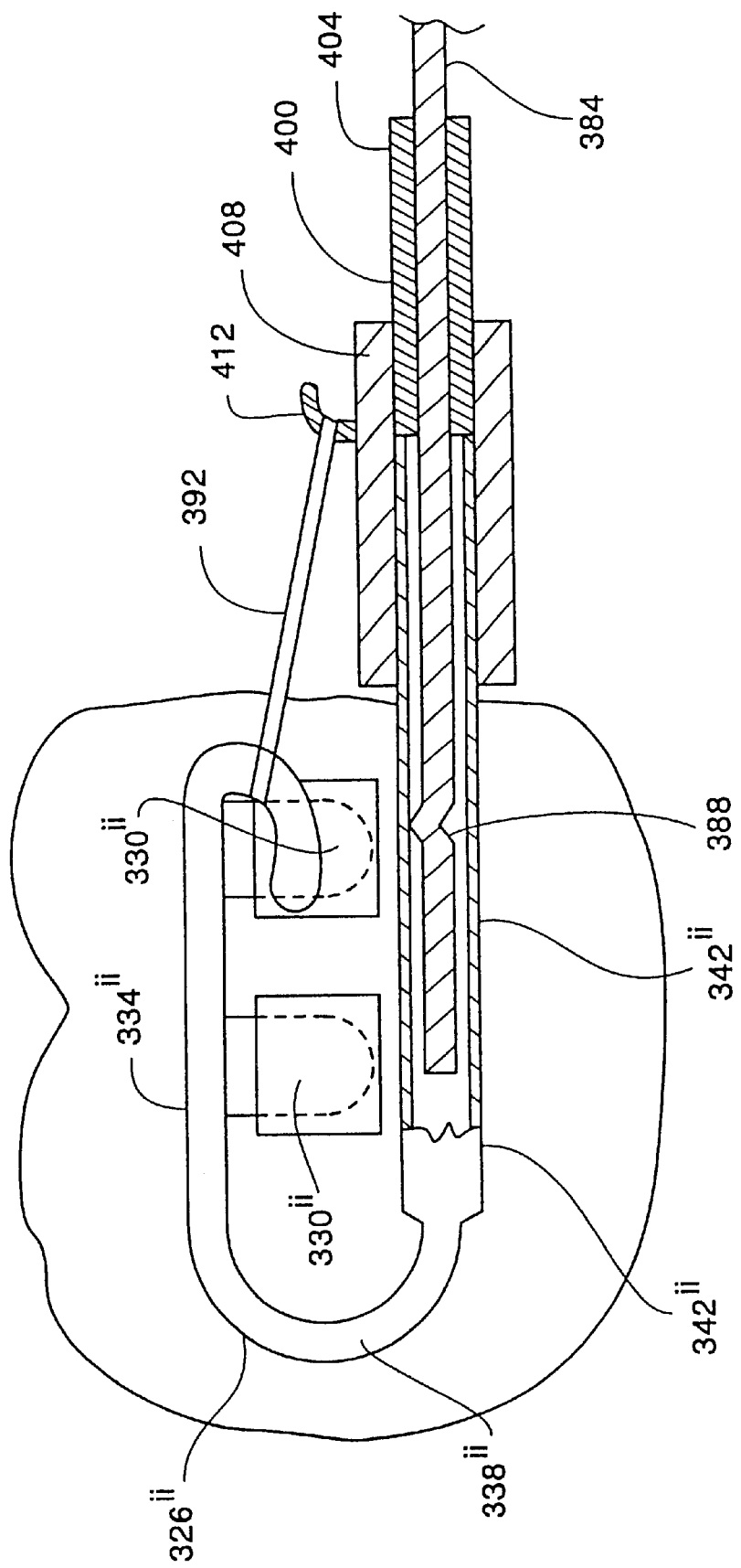
FIG. 16 is a cross-sectional view (looking labially) of another embodiment of an orthodontic connector, such as for a lingual arch developer.

Another embodiment of a ligature assembly which may be used with the connector 326$^{ii}$, as well as all other connectors described herein, is illustrated in FIG. 16. The ligature assembly 400 allows for the above-described types of lingual arch developers to be ligated to the connector 326$^{ii}$ without providing any resistance to the mesial advancement of the lingual arch for a predetermined amount of mesial advancement of the lingual arch. The ligature assembly 400 generally includes a stop tube 404 which in the illustrated embodiment is generally cylindrical and hollow. An outer sleeve 408 is disposed partially over the distal end of the stop tube 404, extends distally from the stop tube 404, and is appropriately secured to the stop tube 404 (e.g., laser welding, brazing). The inner diameter of the outer sleeve 408 is selected to be larger than the outer diameter of the third segment 342$^{ii}$ of the connector 326$^{ii}$ such that it may be slidably associated therewith but with sufficient stability.

The ligature assembly 400 is disposed mesially of the connector 326$^{ii}$ such that the outer sleeve 408 extends over the hollow third segment 342$^{ii}$ and the distal end of the stop tube 404 engages the mesial end of the third segment 342$^{ii}$. A ligature 392 (e.g., elastic, metal) may then engage the hook 364 on the connector 326$^{ii}$ and extend down into engagement with the tiehook 412 attached to the outer sleeve 408 of the ligature assembly 400. The ligature 392 may be exerting at least a distally directed force on the stop tube 404 to maintain engagement between the stop tube 404 and the third segment 342$^{ii}$ of the connector 326$^{ii}$. However, since the lingual arch 384 is slidable relative to the stop tube 404, as well as the outer sleeve 408 and the third segment 342$^{ii}$ of the connector 326$^{ii}$, no resistance is provided to mesial movement of the lingual arch 384 relative to the connector 326$^{ii}$ until the lingual arch 384 has advanced a certain predetermined amount relative to the connector 326$^{ii}$. That is, once the lingual arch 384 has advanced such that the crimp 388 engages the distal end of the stop tube 404, the ligature 392 will begin to oppose further mesial movement of the lingual arch 384 as in the above-described embodiment.

Figure 17A:
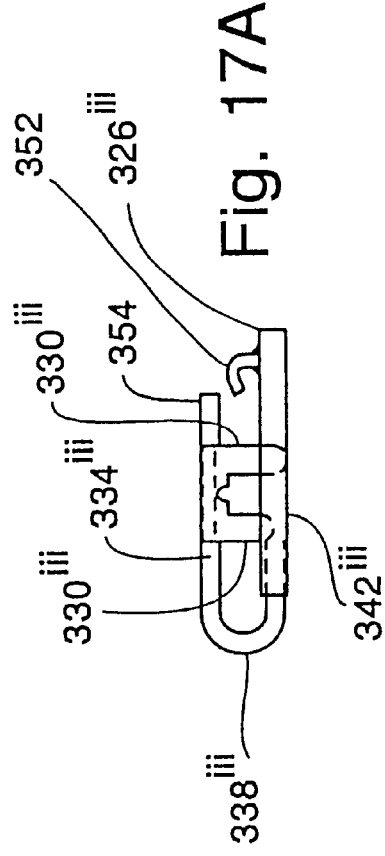
FIGS. 17A–C are views of another embodiment of an orthodontic connector for providing an interface between a tooth and an orthodontic appliance, such as a lingual arch developer.
Figure 17C:
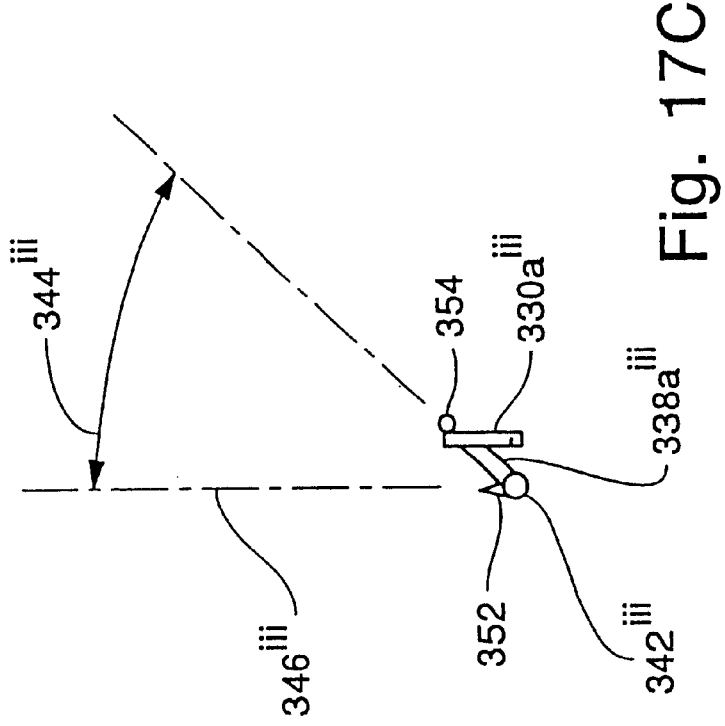
Figure 17B:
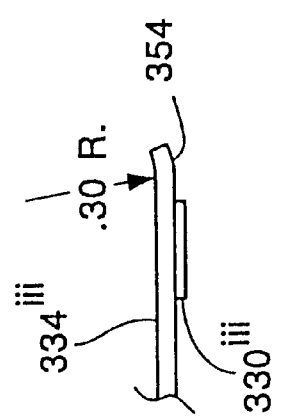

Another embodiment of a connector which may be utilized with each of the above-described lingual arch developers and/or ligature assemblies, as well as a variety of other orthodontic appliances, is illustrated in FIGS. 17A–C. The connector 326$^{iii}$ is generally similar to the connectors 326, 326$^{i}$, and 326$^{ii}$ discussed above. corresponding structure is similarly numbered, and a superscripted "iii" designation is used. The connector 326$^{iii}$ includes a pair of generally occlusal-gingivally extending, mesio-distally spaced posts 330$^{iii}$, a generally distally extending first segment 334$^{iii}$, a generally semi-circular second segment 338$^{iii}$, and a generally mesially extending third segment 342$^{iii}$ which is again lingually offset in a lingual application. The posts 330$^{iii}$ are actually disposed generally within the occlusal-gingivally extending reference plane 346$^{iii}$, but may be disposed at a relatively small angle 348 (e.g., 10°) relative to this reference plane 346$^{iii}$ (e.g., the tips of the posts 330$^{iii}$ being disposed more lingually). This is within the meaning of "generally occlusal-gingivally extending" in relation to the orientation of the posts of the connector and their corresponding lingual tubes on the band.

The connector 326$^{iii}$ also includes a number of additional advantageous features. The connector 326$^{iii}$ includes a hook 352 which is disposed on the mesial end of the third segment 342$^{iii}$ and opens or faces generally distally. Having the hook 352 in this position versus as an extension off of the first segment as in the case of the connectors 326 and 326$^{ii}$ reduces the potential for food becoming trapped in the connector 326$^{iii}$. As such, it should be appreciated that the connectors 326 and 326$^{ii}$ could also utilize a similarly configured and positioned hook 352 instead of the hooks described with such embodiments.

The connector 326$^{iii}$ also includes an extension 354 which extends mesially from the first segment 334$^{iii}$ beyond the mesial post 330$a^{iii}$ and is a cantilever in that it has a free, unsupported mesial end. Preferably, the extension 354 is integrally formed with the first segment 334$^{iii}$. Having the extension 354 extend a certain distance beyond the mesial post 330$a^{iii}$ assists in the installation and/or removal of the connector 326$^{iii}$ from the associated band having the pair of generally occlusal-gingivally extending lingual tubes. In one embodiment, the extension 354 extends about 0.120 inches (about 3 mm) beyond the mesial post 330$a^{iii}$. The extension 354 is also curved to generally approximate the contour of the tooth on which the connector 326$^{iii}$ is disposed (i.e., the free end of the extension 354 curves inwardly toward the tooth). This further facilitates the extension's 352 functioning as a handle (e.g., for interfacing with a Howe pliers), as well as reducing the potential for the trapping of food. In one embodiment this curvature is defined by a radius of about 0.30 inches (7.62 mm).

Stability during relative movement between the lingual arch and the horizontal tube of the above-described connectors is desirable for treatment. This may be realized through use of the end section 356 illustrated in FIG. 18A. The end section 356 is effectively a hollow tube having a hook 358 on its mesial end. The inner diameter of the end section 356 is sized such that it will receive the distal end of a lingual arch. One way in which the lingual arch may be substantially rigidly connected to the end section 356 is to place bends in the distal end of the lingual arch that "catch" on the interior of the end section 356 when sliding there-through. The outer diameter of the end section 356 is selected to be slidably received in the horizontal tube of the noted connectors, for instance the third segment 342$^{iii}$ of the connector 326$^{iii}$. Preferably, there will be an appropriate annular gap between the outer surface of the end section 356 and the inner surface of the third segment 342$^{iii}$ (e.g., 0.002 inch to 0.004 inch annular gap).

The end section 356 and its hook 358 also allows for the use of a ligature assembly with a lingual arch of a lingual arch developer. Referring to FIG. 18B, a ligature assembly 444 includes the above-described end section 356 and an appropriate ligature 448 (e.g., metal ligature, elastic). The lingual arch 450 is appropriately secured to the end section 356. An appropriate force generating member 454 is disposed over or about the distal end of the end section 356, and the distal end of the end section 356 is disposed within the third segment 342$^{iii}$. This disposes the force generating member 454 between the hook 352 and the hook 358 such that the force generating member 454 can apply generally mesially-directed forces to the end section 356 and the lingual arch 450 fixedly interconnected therewith.

The ligature 448 extends between the hook 352 on the third segment 342$^{iii}$ and the hook 358 on the end section 356. The ligature 448 is illustrated as being in a relatively taut condition. Forces which counteract those being applied to the lingual arch 450 by the force generating member 454 are thereby being generated/applied by the ligature 448 to the lingual arch 450. This may be desirable in some cases such as when the force generating member 454 has the ability to apply more than the desired force to the lingual arch 450. The ligature 448 also functions to reduce the potential for the end section 356, and thus the lingual arch 450, becoming disengaged with the connector 326$^{iii}$, and thus provides a safety enhancement feature.

The ligature 448 may have a variety of characteristics which provide for and/or contribute to the generation of counteracting force and/or the provision of safety features. Initially, the ligature 448 may be such that no counteracting forces are applied to the mesial advancement of the lingual arch 450 until treatment has progressed a predetermined amount. This may be affected by using a metal ligature 448 of an appropriate length (e.g., such that there is some slack in the ligature 448 in the beginning of treatment, but which becomes taut after a predetermined amount of mesial advancement of the lingual arch 450 to completely counteract the abilities of the force generating member 454). The ligature 448 may also be such that the counteracting forces which it applies to the lingual arch 450 increase in some fashion during mesial advancement of the lingual arch 450 (e.g., such that it applies increasing counteracting forces as treatment progresses).

The ligature 448 may provide a function in addition to those presented above by the way in which the ligature 448 is installed. Continuing to refer to FIG. 18B, the ligature 448 may engage the hook 352 and then wrap around the mesial portion of the third segment 342$^{iii}$ and then the end section 356 in generally helical fashion for engagement with the hook 358. Torsional forces are generated by this positioning of the ligature 348 and these forces are applied to the tooth on which the connector 326$^{iii}$ is disposed. This is advantageous when the lingual arch 450 is also being used for transverse movement of the patient's arch (e.g., expansion). Expansion of the arch may result in a degree of transverse movement of the crown(s) of the various teeth which is different than that of the root(s) of the various teeth which results in an undesired torquing of the tooth. An example would be the crown of a given tooth "tipping" away from the patient's midline during transverse arch expansion, with the root of this tooth actually "tipping" toward the patient's midline. The above-described wrapping of the ligature 448 actually generates forces which are applied to the third segment 342$^{iii}$ to counteract this type of movement of the associated tooth which keeps the tooth more upright during outward movement (e.g., the ligature 448 achieves a more bodily movement of the tooth interconnected with the connector 326$^{iii}$). Wrapping the ligature 448 in one direction will apply these torsional forces in one direction, while wrapping the ligature 448 in the opposite direction will apply these torsional forces in the opposite direction. Although various ligatures 448 may be used to provide this torquing function, elastics are believed to be preferred. Representative elastics for use as a ligature 448 are illustrated in FIG. 18C and are commercially available from the assignee of this patent application and referred to as "Energy-chain™" Elastics.

Alternatively, the force generating device illustrated in FIGS. 1–6 can be employed to exert torsional forces in one or another direction. This can be accomplished by twisting the elastomeric member in a first direction. The memory of the elastomeric member will cause the member to exert a force in the direction opposite to which it is twisted in order to return to its original undeformed configuration. The amount of force exerted can be regulated by the amount the elastomeric member is twisted prior to placing the free end over the second of the two collars. The twisting is preferably accomplished before the two ends of the elastomeric members are placed over the respective collars. For example, one end of the elastomeric member can be placed over one collar, the elastomeric member can be twisted and then the other end can be placed over the other collar. Due to the memory of the elastomeric material, the member will exert a force in the attempt to return to its original undeformed configuration, thereby exerting a torsional force which can be transferred to the tooth to which the force generating member is anchored. In another embodiment, tipping can be reduced or eliminated by reducing or eliminating relative motion between the first collar and the second collar. One way to accomplish this is to employ cross-sectional configurations for the piston and the orifice which do not allow relative rotational motion. For example, the piston and orifice can be mating, non-circular cross-sectional configurations (e.g. square, rectangle, triangle, star-shaped, oval, polygonal, etc.). In this manner, the first collar would be prevented from rotating relative to the second collar, thereby reducing or eliminating tipping of the tooth to which the first collar is attached.

Another embodiment of a connector which may be utilized with each of the above-described lingual arch developers and/or ligature assemblies is illustrated in FIGS. 19A–B. The connector 326$^{iv}$ is generally similar to the connectors 326, 326$^{i}$, 326$^{ii}$, and 326$^{iii}$ discussed above and corresponding structure is identified by a superscripted "iv" designation. The connector 326$^{iv}$ includes a pair of generally occlusal-gingivally extending, mesio-distally spaced posts 330$^{iv}$, a generally distally extending first segment 334$^{iv}$, a generally semicircular second segment 338$^{iv}$, and a generally mesially extending and lingually offset third segment 342$^{iv}$. The posts 330$^{iv}$ may also be disposed in the manner discussed above in relation to the posts 330$^{iii}$.

The connector 326$^{iv}$ also includes a number of additional advantageous features. The connector 326$^{iv}$ includes a hook 352$^{iv}$ which is disposed on the mesial end of the third segment 342$^{iv}$ and opens generally distally as in the case of the connector 326$^{iii}$. The connector 326$^{iv}$ also includes an extension 416 which extends mesially from the first segment 334$^{iv}$ and is a cantilever in that it has a free end 418. The length of the extension 416 is selected such if it was adapted to the lingual of a patient's dentition (i.e., the extension 416 may be bent to generally conform to the lingual of a patient's dentition), the end 418 of the extension 416 would be disposed preferably slightly beyond the midline (FIG. 20B) of the patient's arch (e.g., at the distal of the opposite lateral tooth). In one embodiment, the extension 416 will typically extend between about 55 mm and about 65 mm beyond the mesial-most post 330a$^{iv}$. The orthodontic practitioner or lab may adapt the extension 416 to the application with which it is being used. This may entail bending the extension 416 and/or shortening the extension 416 by cutting off a portion of its length from the mesial end thereof.

One use of the connector 326$^{iv}$ and its extension 416 is as a mounting frame of sorts for bite blocks. This application is illustrated in FIGS. 20A–B in which the connector 326$^{iv}$ is mounted on a lower first molar and in which the bite block is illustrated in dashed lines (FIG. 20A). A band (not shown) is mounted on the first molar and has a pair of generally occlusal-gingivally extending lingual tubes 468 and a generally mesio-distally extending buccal tube 464. In order to adapt the connector 326$^{iv}$ for this bite block mounting application, the mesial extension 416 is bent into a generally U-shaped configuration. The extension 416 is bent into a first section 420 which extends generally mesially of the mesial post 330a$^{iv}$ of the connector 326$^{iv}$, a second section 424 which extends up and over the dentition (in the illustrated embodiment up and over the second bicuspid), and a third section 428 which extends distally from the second section 424 to interface with the buccal tube 440. When installing the connector 326$^{iv}$, the free end 418 of the extension 416 slides through the buccal tube 440 and each of the posts 330$^{iv}$ is disposed in the associated lingual tube 468. The end 418 of the extension 416 may then be bent to further rigidly interconnect the connector 326$^{iv}$ with the patient's tooth (typically occlusally or gingivally).

When adapting the extension 416 to this bite block mounting application, the extension 416 is bent into the above-described configuration typically using a stone model of the orthodontic patient. Thereafter, the bite block is mounted on the reconfigured extension 416. In the case in which the connector 326$^{iv}$ is used with a bite block, the second section 424 is disposed in the preformed portion of the bite block. Typically, this is done by molding (e.g., insert, injection) the preformed portion about the second section 424. An enhanced interlocking relationship between the connector 326$^{iv}$ and the bite block may be realized by bending the second section 424 into the illustrated configuration of FIG. 20A prior to "installing" the bite block thereon.

Other uses of the extension 416 of the connector 326$^{iv}$ involve adapting the extension 416 to the lingual of the patient's dentition. In one application in which this lingual adaptation is provided, a portion of the extension 416 mesial of the posts 330$^{iv}$ is bent into an "omega" configuration 417 which is illustrated in FIG. 21 and the function of which is discussed in more detail in U.S. Pat. No. 4,354,834, entitled "Modular Orthodontic Appliances, and issued Oct. 19, 1982. The entire disclosure of U.S. Pat. No. 4,354,834 is incorporated by reference in its entirety herein. Portions of the extension 416 disposed mesially of the omega 417 are then bent to conform to the lingual shape of the arch. By similarly configuring the extension 416 of the connector 326$^{iv}$ disposed on the opposite side of the patient's mouth, portions of the two extensions 416 will be in an overlapping relation generally at/about the midline 460 (FIG. 20B) of the corresponding dentition. The overlapping portions of the two extensions 416 may then be joined together at the overlapping interface (e.g., via brazing). With this configuration, the omega 417 of one or both of the extensions 416 may be activated in a variety of ways as described in U.S. Pat. No. 4,354,834 to provide/generate the desired type of orthodontic treatment force. The third segment 342$^{iv}$, of course, is available for use by interfacing with other orthodontic appliances at the same type which may beneficially interact with the forces being generated by the joined extensions 416.

Another configuration of the connector 326$^{iv}$ when the extension 416 is adapted to the patient's lingual is to conform the extension 416 to the patient's lingual and leave the two ends 417 of the two extensions 416 unconnected. In this case the extensions 416 would remain independently active which may be desirable if there is a need for a significant amount of advancement of anterior teeth.

Another use for the connector 326$^{iv}$ is to utilize the extensions 416 as a mounting for establishing anchorage on the forward portion of the patient's mouth. For instance, with the connectors 326$^{iv}$ being installed on the patient's upper arch (in an inverted position to that illustrated in FIG. 19A), the extensions 416 could be cocked upwardly at an angle of about 30° such that the free ends of the two extensions 416 would be disposed at the front part of the patient's palate. With free end portions of the extensions 416 being in an overlapping relation in this location, an acrylic button or the like (e.g., a Nance button) may be molded around the free end portions of the extensions 416. The acrylic is molded on a stone casting of the patient and will be in general conforming engagement with the patient when installed. With the connectors 326$^{iv}$ being disposed on the patient's upper first molars, this will allow other orthodontic appliances to interface with the upper first molars without affecting movement of the upper first molars due to the anchorage provided by the above-described extensions 416. For instance, elastics may be mounted on the buccal of the upper first molars and extend to teeth of the patient's lower dentition to apply an orthodontic treatment force thereto without having any significant effect on the position of the upper first molars since they are maintained in a fixed position by the above-described frontal anchorage provided by the extensions 416. The connectors 326$^{iv}$ of course may also be installed on the lower arch and provide this type of forward anchorage by having the ends 418 of the mesial extensions 416 be disposed below the patient's gum line on the forward portion of the lower dentition.

Yet another use for the connector 326$^{iv}$ is to utilize the extension 416 for interfacing with other orthodontic appliances. When a connector 326$^{iv}$ is installed on the patient's upper arch, (the position of the connector 326$^{iv}$ then being inverted from that illustrated in FIG. 19A), the extension 416 may be bent upwardly at an angle of about 90° such that the end 418 is at the vault of the patient's palate. The free end 418 of the extension 416 may then interface with a palatal expansion appliance (e.g., devices which achieve transverse arch width).

Figure 22A:
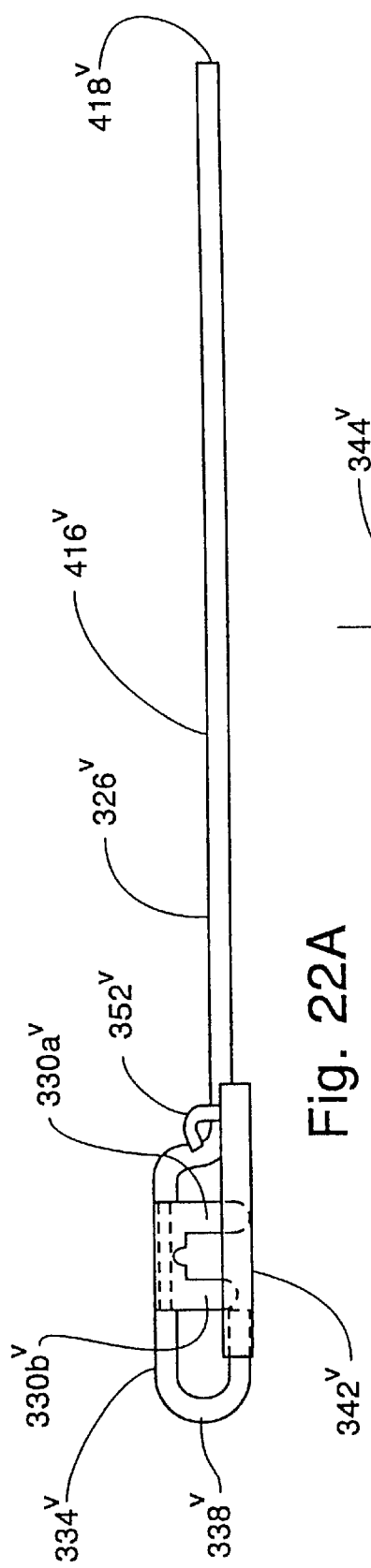
FIGS. 22A–B are views of another embodiment of a connector for providing an interface between a tooth and an orthodontic appliance, such as a lingual arch developer.
Figure 22B:
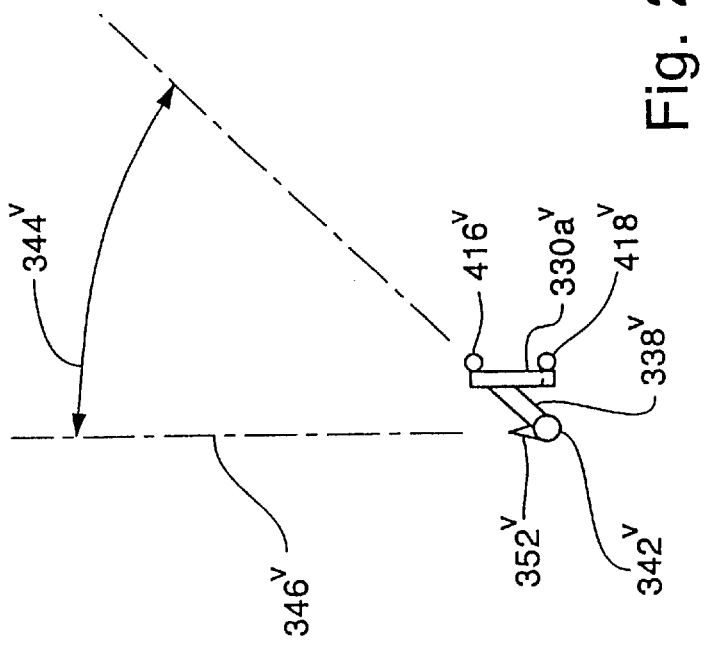

Another embodiment of a connector which may be utilized with each of the above-described lingual arch developers and/or ligature assemblies is illustrated in FIGS. 22A–B. The connector 326$^{v}$ is generally similar to the connectors 326, 326$^{i}$, 326$^{ii}$, 326$^{iii}$, and 326$^{iv}$ discussed above and corresponding structure is similarly numbered and identified by a superscripted "v" designation. The connector 326$^{v}$ includes a pair of generally occlusal-gingivally extending, mesio-distally spaced posts 330$^{v}$, a generally distally extending first segment 334$^{v}$, a generally semi-circular second segment 338$^{v}$, and a generally distally extending and lingually offset (for a lingual application) third segment 342$^{v}$. The posts 330$^{v}$ may also be disposed similar to the posts 330$^{iii}$ discussed above.

The connector 326$^{v}$ also includes a number of additional advantageous features. The connector 326$^{v}$ includes a hook 352$^{v}$ which is disposed on the mesial end of the third segment 342$^{v}$ and opens generally distally as in the case of the connector 326$^{iv}$. The connector 326$^{v}$ also includes an extension 416$^{v}$ which is interconnected with the first segment 334$^{v}$ and extends gingivally and then mesially beyond the mesial post 330$a^{v}$. The extension 416$^{v}$ is cantilevered in that it includes a free end 418$^{v}$. The length of the extension 416$^{v}$ is selected such if it was adapted to the lingual of a patient's dentition (i.e., the extension 416$^{v}$ may be bent to generally conform to the lingual of a patient's dentition), the end 418$^{v}$ of the extension 416$^{v}$ would be disposed preferably slightly beyond the midline of the arch (e.g., at the distal of the opposite lateral tooth). Therefore, the extension 416$^{v}$ is sized similarly to the extension 416 discussed above. Although the extension 416$^{v}$ may have a variety of uses, typically it will be used in the case where the extension 416$^{v}$ is adapted to the lingual of the patient's dentition and put into overlapping relation with an extension 416$^{v}$ disposed on the opposite side of the patient's arch, all as discussed above with regard to the extension 416$^{v}$.

Another embodiment of a lingual arch developer is illustrated in FIG. 23. The lingual arch developer 472 is illustrated as being interconnected with the orthodontic patient by the connector 326$^{iii}$ and an end section 356. Another connector 326$^{iii}$ and end section 356 would of course be disposed on the opposite side of the patient's jaw. It will be appreciated that the lingual arch developer 472 may be used with other connectors described herein which would allow the lingual arch developer 472 to advance the patient's arch in the above-described manner.

The lingual arch developer 472 includes a lingual arch 476 which engages the lingual surface of the patient's dentition defining the patient's arch. The first distal section 478 interfaces with the connector 326$^{iii}$ via the end section 356 similar to that described above. That is, the first distal section 478 is fixedly attached to the end section 356 such that the lingual arch 476 and the end section 356 move together simultaneously (e.g., by bending a portion of the first distal section 478 and disposing this bent portion within the interior of the end section 456 to fix the end section 356 relative to the lingual arch 476 as discussed above). The end section 356 then slidably interfaces with the third segment 342$^{iii}$ of the connector 326$^{iii}$.

An aspect of the present invention relates to developing an orthodontic patient's arch from the lingual. A lingual arch is slidably interconnected with the lingual of the patient's arch. At least two magnets are utilized to have some type of effect on the movement of the lingual arch during development of the patient's arch. Mesial advancement of the lingual arch and therefore the patient's arch may be affected at least in part by these two magnets, such as through using magnets whose respective magnetic fields generate repulsive forces such that the magnets repel or move away from each other. The magnets may be the sole source for generating the generally mesially-directed forces applied to the lingual arch, or may be used in conjunction with one or more other force-generating members (e.g., springs, elastomers). Magnets whose respective magnetic fields generate an attraction between the magnets may also be used to retard the mesial advancement of the lingual arch by biasing the magnets toward each other. This may be utilized to reduce the magnitude of mesially-directed forces being applied to the lingual arch by the force-generating member(s) (e.g., to reduce the effect which a compressed spring has on the lingual arch).

In one embodiment of this aspect, a first of the magnets is maintained in a fixed position while a second of the magnets is associated and moves with the lingual arch during development of the patient's arch. Maintaining the first magnet in a fixed position allows the first magnet to provides an anchoring-like function for movement of the second magnet which has some type of effect on the movement of the lingual arch. This may be affected by attaching the first magnet to a connector associated with one of the patient's teeth and which is used to provide an interface between the lingual arch and the orthodontic patient (e.g., the connector discussed above in the first aspect of the present invention), or otherwise such that it remains substantially stationery relative to the mesially-advancing lingual arch and/or the orthodontic patient.

Association of the second magnet with the lingual arch may be realized by attaching the second magnet to the lingual arch or structure which also moves with the lingual arch (e.g., an end section which is fixed to be lingual arch and which slidably interfaces with the connector of the first aspect). Treatment options which are available with this type of interconnection include using magnets as the sole source for the mesially-directed forces applied to the lingual arch and using magnets to retard or resist the mesial advancement of the lingual arch provided by the force-generating member (s) which mesially advance the lingual arch and thereby the patient's arch. The second magnet may also be movably interconnected with the lingual arch or structure which also moves with the lingual arch (e.g., an end section which is fixed to be lingual arch and which slidably interfaces with the connector of the first aspect). This will typically be utilized when additional force-generating members are being used. For instance, a spring may be disposed between this second magnet and a stop associated with the lingual arch (e.g,. a hook attached to an end section which is fixed to an end or end portion of the lingual arch). As the second magnet moves mesially relative to the first magnet, the magnitude of the repulsive forces therebetween is reduced. However, this mesial movement of the second magnet will maintain the spring in a certain state of compression such that the magnitude of forces being applied to the lingual arch remain within a certain desired range for a certain period of time.

The lingual arch developer 472 includes at least one force-generating member for exerting a generally mesially-directed force on the lingual arch 476, and thereby the lingual surface of the patient's dentition which defines the arch undergoing development. In the illustrated embodiment, the force-generating member is actually a system including a first magnet 480, a second magnet 484, and a spring 488. Typically, the same type of configuration would be provided on the other side of the lingual arch 476 as well such that symmetrical forces are applied to the lingual arch 476.

The first magnet 480 is maintained in a fixed position relative to the connector 326$^{iii}$ and the end section 356. This may be affected by fixedly attaching the first magnet 480 to the mesial end of the third segment 342$^{iii}$ of the connector 326$^{iii}$ (e.g., by a butt joint) or the mesial end portion of the third segment 342$^{iii}$ (e.g., by disposing the first magnet 480 about the third segment 342$^{iii}$). Various alternatives exist for maintaining this fixed attachment, including being potted in acrylic or in a metallic sheath. The second magnet 484 interfaces with the end section 356 in a manner discussed below and is positioned between the first magnet 480 and the spring 488. One end of the spring 488 engages the second magnet 484, while the other end of the spring engages the hook 358 on the end section 356.

As noted, the magnets 480 and 484 are part of a system which is at least one of the force-generating member(s) used by the lingual arch developer 472. In the illustrated embodiment, the magnets 480 and 484 are repulsive in that the interaction of the magnetic fields of the magnets 480 and 484 move the second magnet 484 mesially away from the first magnet 480. Again, the first magnet 480 remains in a fixed position to provide an anchoring function for movement of the second magnet 484. The second magnet 484 is movably interconnected with the end section 356 in that it is able to slide relative to the exterior surface of the end section 356. This is provided in the illustrated embodiment by utilizing a generally cylindrical or doughnut-shaped configuration for the second magnet 484 as illustrated in FIG. 24. As the second magnet 484 moves along the end section 356, the distance between the magnets 480 and 484 increases. Increasing the distance between the first magnet 480 and the second magnet 484 will of course reduce the magnitude of the repulsive forces therebetween. However, the movement of the second magnet 484 along the exterior of the end section 356 also maintains the spring 488 in compression. As a result, the combinative forces applied to the lingual arch 276 remain within a desired range for a desired period of time.

It may be possible to use the magnets 480 and 484 as the sole source of the generally mesially-directed forces applied to the lingual arch 476 in certain applications (not shown). The second magnet 284 would be fixedly attached to the end section 356 and its magnetic field would interact with the magnetic field of the first magnet 480. Due to the first magnet 480 being fixedly attached to the connector 326$^{iii}$, the second magnet 484 advances mesially away from the first magnet 480. This movement of the second magnet 484 similarly mesially advances the lingual arch 476 to develop the patient's arch.

The magnets 480 and 484 may also be used to reduce the amount of forces being applied to the lingual arch 472 by another portion of the force-generating system. This would be desirable, for instance, when undesirably strong mesially-directed forces are being transmitted to the lingual arch 476 by this part of the force-generating system. Attractive forces would be utilized between the first magnet 480 and the second magnet 484 in this instance. Specifically, the interaction of the magnetic fields of the first magnet 480 and the second magnet 484 would bias the second magnet 484 distally toward the first magnet 480 which is again maintained in a fixed position relative to the lingual arch 476. In order to affect this type of "tethering-like" function, the second magnet 484 would be fixedly attached to the end section 356 (not shown). This type of configuration would be desirable if, for instance, the spring 488 exerted more forces than desired on the lingual arch 476.

A variety of magnetic materials may be utilized for the first magnet 480 and the second magnet 484. Preferred materials for the magnets 480 and 484 include the rare earth metals since such materials provide desired properties for this orthodontic treatment application. Rare earth magnets generate strong magnetic fields and retain their magnetic field for a desired period of time. These strong magnetic fields may be obtained through use of relatively small sized magnets. Various configurations may also the utilized in the case of rare earth magnets. Rare earth magnets are also not bipolar. Preferred rare earth materials for the magnets 480 and 484 include neodynium/boron and sararium/cobalt.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. For example, the various elements of the assemblies described herein can be used in different configurations. Specifically, the force generating device employing an elastomeric member can be substituted for force generating devices employing springs or other members in the embodiments described herein. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A force generating device comprising:
   (a) an elastomeric member;
   (b) a first collar for receiving a first end of said elastomeric member;
   (c) a second collar for receiving a second end of said elastomeric member;
   (d) an orifice for receiving a piston wherein said orifice is operationally attached to said first collar; and
   (e) a piston which is slidably engageable into said orifice wherein said piston is operationally attached to said second collar; wherein when said force generating device is assembled, said elastomeric member operationally connects said first collar and said second collar and wherein said piston is slidably engaged within said orifice.

2. The force generating device of claim 1, wherein said elastomeric member is an elastomeric polymer tube having one end which frictionally engages the outer surface of said first collar and having a second end which frictionally engages the outer surface of said second collar.

3. The force generating device of claim 2, wherein said first collar and said second collar have ribbed outer surfaces in order to enhance the frictional engagement between inner surfaces of said elastomeric polymer tube and said outer ribbed surfaces of said collars.

4. The force generating device of claim 2, wherein said first collar includes a first end stop and said second collar includes a second end stop and wherein said one end of said elastomeric polymer tube is limited in axial movement by said first end stop whererin said second end of said elastomeric polymer tube is limited in axial movement by said second end stop.

5. The force generating device of claim 1, further comprising a connector for interconnecting said force generating device with a tooth of a patient, said connector comprising:
   (i) means for attaching said connector to a tooth;
   (ii) a first segmrnt extending at least distally from said means for attaching;
   (iii) a second segment interconnected with said first segment and extending at least gingivally from said first segment; and
   (iv) a third segment interconnected with said second segment and extending at least mesially from said second segment.

6. The device of claim 5, wherein said means for attaching said connector to a tooth comprises:
   (a) a band adapted to be attached to a tooth of a patient, said band having a first band tube attached thereto; and
   (b) first post slidably interconnectable with said first band tube.

7. The force generating device of claim 1, wherein said force generating device is part of an application selected from the group consisting of lingual arch developers, labial arch developers and distallizing appliances.

8. The force generating device of claim 1, wherein said second collar is operationally attached to an arch wire.

9. A device comprising:
   (a) an elastomeric member;
   (b) a first collar for receiving a first end of said elastomeric member;
   (c) a second collar for receiving a second end of said elastomeric member;
   (d) an orifice for receiving a piston wherein said orifice is operationally attached to said first collar;
   (e) a piston which is slidably engageable into said orifice wherein said piston is operationally attached to said second collar; wherein when said force generating device is assembled, said elastomeric member operationally connects said first collar and said second collar and wherein said piston is slidably engaged within said orifice; and
   (f) a connector for interconnecting a force generating device of (a), (b), (c), (d) and (e) with a tooth of a patient, said connector comprising:
      (i) means for attaching said connector to a tooth;
      (ii) a first segment extending at least distally from said means for attaching;
      (iii) a second segment interconnected with said first segment and extending at least gingivally from said first segment; and
      (iv) a third segment interconnected with said second segment and extending at least mesially from said second segment.

10. The device of claim 9, wherein said device is part of an appliance selected from the group consisting of lingual arch developers, labial arch developers and distallizing appliances.

11. The device of claim 9, wherein said means for attaching said connector to a tooth comprises:
   (a) a band adapted to be attached to a tooth of an orthodontic patient, said band having a first band tube attached thereto; and
   (b) a first post slidably interconnectable with said first band tube.

12. A method for generating a force comprising the steps of:
   (a) providing an elastomeric member;
   (b) providing a first collar comprising an orifice which is operationally attached to said first collar;
   (c) providing a second collar comprising a piston which is operationally attached to said second collar;
   (d) placing said piston in said orifice;

(e) placing a first end of said elastomeric member on said first collar;

(f) placing a second end of said elastomeric member on said second collar; and (g) deforming said elastomeric member in order to create a force.

13. The method of claim 12, wherein said deformation comprises compressing said elastomeric member in order to create an expansive force.

14. The method of claim 12, wherein said deformation comprises twisting said elastomeric member in order to create a torsional force.

15. The method of claim 12, wherein at least one of said first collar and said second collar is operationally connected to a tooth.

16. The method of claim 12, wherein said force is generated in connection with a appliance selected from the group consisting of lingual arch developers, labial arch developers and distallizing appliances.

17. The method of claim 16, wherein said force is a generally mesially-directed force on the lingual arch of a patient.

18. The method of claim 16, wherein the ends of a lingual arch are compressed toward each other and operationally interconnected with at least one of said first collar and said second collar such that said arch exerts an expansive force on a patient's corresponding dentition.

19. The method of claim 12, wherein said force is applied to an arch wire.

20. The method of claim 12, wherein said force is generated in conjunction with a connector.

\* \* \* \* \*